United States Patent
Baumann et al.

(10) Patent No.: US 11,179,390 B2
(45) Date of Patent: Nov. 23, 2021

(54) SUBCUTANEOUS ADMINISTRATION OF A P2Y$_{12}$ RECEPTOR ANTAGONIST

(71) Applicant: Idorsia Pharmaceuticals Ltd, Allschwil (CH)

(72) Inventors: Martine Baumann, Allschwil (CH); Markus Kramberg, Allschwil (CH); Markus Rey, Allschwil (CH); Markus Riederer, Allschwil (CH); Sebastien Roux, Allschwil (CH)

(73) Assignee: Idorsia Pharmaceuticals Ltd, Allschwil (CH)

( * ) Notice: Subject to any disclaimer, the term of this patent is extended or adjusted under 35 U.S.C. 154(b) by 61 days.

(21) Appl. No.: 16/494,254

(22) PCT Filed: Mar. 14, 2018

(86) PCT No.: PCT/EP2018/056372
§ 371 (c)(1),
(2) Date: Sep. 13, 2019

(87) PCT Pub. No.: WO2018/167139
PCT Pub. Date: Sep. 20, 2018

(65) Prior Publication Data
US 2020/0129510 A1   Apr. 30, 2020

(30) Foreign Application Priority Data
Mar. 15, 2017 (WO) ................. PCT/EP2017/056175

(51) Int. Cl.
*A61K 31/506* (2006.01)
*A61P 7/02* (2006.01)
*A61K 9/00* (2006.01)

(52) U.S. Cl.
CPC .......... *A61K 31/506* (2013.01); *A61K 9/0021* (2013.01); *A61P 7/02* (2018.01)

(58) Field of Classification Search
CPC ................................ A61K 31/502; A61P 7/02
See application file for complete search history.

(56) References Cited

U.S. PATENT DOCUMENTS

| | | |
|---|---|---|
| 3,870,035 A | 3/1975 | Sarnoff |
| 4,004,577 A | 1/1977 | Sarnoff |
| 4,795,433 A | 1/1989 | Sarnoff |
| 5,078,680 A | 1/1992 | Sarnoff |
| 6,855,715 B1 | 2/2005 | Liebeschuetz et al. |
| 8,044,055 B2 | 10/2011 | Caroff et al. |
| 8,048,881 B2 | 11/2011 | Caroff et al. |
| 8,058,263 B2 | 11/2011 | Caroff et al. |
| 8,067,419 B2 | 11/2011 | Binkert et al. |
| 8,093,250 B2 | 1/2012 | Caroff et al. |
| 8,288,385 B2 | 10/2012 | Caroff et al. |
| 8,466,156 B2 | 6/2013 | Caroff et al. |
| 8,518,912 B2 | 8/2013 | Caroff et al. |
| 8,664,203 B2 | 3/2014 | Caroff et al. |
| 2003/0060474 A1 | 3/2003 | Bryant et al. |
| 2005/0038037 A1 | 2/2005 | Bryant et al. |
| 2005/0065163 A1 | 3/2005 | Bryant et al. |
| 2008/0194576 A1 | 8/2008 | Caroff et al. |
| 2008/0234272 A1 | 9/2008 | Binkert et al. |
| 2009/0291962 A1 | 11/2009 | Caroff et al. |
| 2010/0035895 A1 | 2/2010 | Caroff et al. |
| 2010/0261678 A1 | 10/2010 | Caroff et al. |
| 2011/0028484 A1 | 2/2011 | Caroff et al. |
| 2011/0046089 A1 | 2/2011 | Caroff et al. |
| 2012/0028989 A1 | 2/2012 | Caroff et al. |
| 2012/0053149 A1 | 3/2012 | Caroff et al. |

FOREIGN PATENT DOCUMENTS

| | | | |
|---|---|---|---|
| EP | 0 407 200 B1 | 1/1994 | |
| JP | 53073586 A | 12/1976 | |
| JP | 2008239617 A | 10/2008 | |
| WO | WO 86/01118 A1 | 2/1986 | |
| WO | WO 86/06965 A1 | 12/1986 | |
| WO | WO 02/098856 A2 | 12/2002 | |
| WO | WO 2004/052366 A1 | 6/2004 | |
| WO | WO 2004/092189 A1 | 10/2004 | |
| WO | WO-2005000281 A2 * | 1/2005 | ......... A61K 31/4152 |
| WO | WO 2006/114774 A2 | 11/2006 | |
| WO | WO 2007/046075 A1 | 4/2007 | |
| WO | WO 2008/044217 A2 | 4/2008 | |

(Continued)

OTHER PUBLICATIONS

Alvinerie et al, "The pharmacokinetics of moxidectin after oral and subcutaneous administration to sheep," *Veterinary Research*, 29(2):113-118 (1998).

Angiolillo et al., "Impact of cangrelor overdosing on bleeding complications in patients undergoing percutaneous coronary intervention: insights from the CHAMPION trials," *J Thromb Thrombolysis*, 40:317-322 (2015).

Aubert et al., "Systemic exposure to parabens: Pharmacokinetics, tissue distribution, excretion balance and plasma metabolites of [14C]-methyl-, propyl- and butylparaben in rats after oral, topical or subcutaneous administration," *Food and Chemical Toxicology*, 50:445-454 (2012).

Barnason et al., "Evidence for Therapeutic Patient Education Interventions to Promote Cardiovascular Patient Self-Management," *Circ Cardiovasc Qual Outcomes*, pp. 1-23 (2017).

Baumann et al., "Effects of Dose and Route of Administration on Pharmacokinetics of (±)-3,4-Methylenedioxymethamphetamine (MDMA) in the Rat," *DMD Fast Forward*, 36 pages (2009).

(Continued)

*Primary Examiner* — Kevin E Weddington
(74) *Attorney, Agent, or Firm* — Hoxie & Associates LLC

(57) ABSTRACT

The present invention relates to a P2Y12 receptor antagonist selected from the group consisting of 4-((R)-2-{[6-((S)-3-methoxy-pyrrolidin-1-yl)-2-phenyl-pyrimidine-4 carbonyl]-amino}-3-phosphono-propionyl)-piperazine-1-carboxylic acid butyl ester, (1S,2S,3R,5S)-3-[7-[(1R,2S)-2-(3,4-difluorophenyl)cyclopropylamino]-5-(propylthio)-3H-[1,2,3]triazolo[4,5-d]pyrimidin-3-yl]-5-(2-hydroxyethoxy)cyclopentane-1,2-diol, and (1S,2R,3S,4R)-4-[7-[(1R,2S)-2-(3,4-difluorophenyl)cyclopropylamino]-5-(propylthio)-3H-[1,2,3]triazolo[4,5-d]pyrimidin-3-yl]cyclopentane-1,2,3-triol, or a pharmaceutically acceptable salt thereof, for use as a medicament by subcutaneous or intradermal administration.

50 Claims, 4 Drawing Sheets

(56) References Cited

FOREIGN PATENT DOCUMENTS

| | | |
|---|---|---|
| WO | WO 2008/050301 A2 | 5/2008 |
| WO | WO 2008/128647 A1 | 10/2008 |
| WO | WO 2008/137753 A2 | 11/2008 |
| WO | WO 2009/069100 A1 | 6/2009 |
| WO | WO 2009/080226 A2 | 7/2009 |
| WO | WO 2009/080227 A2 | 7/2009 |
| WO | WO 2009/125365 A1 | 10/2009 |
| WO | WO 2009/125366 A1 | 10/2009 |
| WO | WO 2010/116328 A2 | 10/2010 |
| WO | WO 2010/122504 A1 | 10/2010 |
| WO | WO 2011/137459 A1 | 11/2011 |
| WO | WO 2011/160768 A1 | 12/2011 |
| WO | WO 2018/055016 | 3/2018 |

OTHER PUBLICATIONS

Bhatt et al., "Intravenous Platelet Blockade with Cangrelor during PCI," *N Engl J Med*, 361:2330-41 (2009).

Bhatt et al., "Effect of Platelet Inhibition with Cangrelor during PCI on Ischemic Events," *N Engl J Med*, 368:1303-13 (2013).

Cerkvenik Flajs et al., "Ivermectin Pharmacokinetics," *Slov Vet Res*, 39(3/4): 167-78 (2002).

Cohen et al., "Plasma Levels of Lidocaine After Intramuscular Administration," *The American Journal of Cardiology*, 29:520-523 (1972).

Collet et al., "Intravenous Clopidogrel (MDCO-157) Compared with Oral Clopidogrel: The Randomized Cross-Over AMPHORE Study," *Am J Cardiovasc Drugs*, 16:43-53 (2016).

Curzen et al., "ST-segment Elevation Myocardial Infarction 2—What is the optimum adjunctive reperfusion strategy for primary percutaneous coronary intervention?," *Lancet;* 382:633-43 (2013).

Gandolf et al., "Pharmacokinetics after intravenous, subcutaneous, and oral administration of enrofloxacin to alpacas," *American Journal of Veterinary Research*, 66(5):767-771 (2005).

Hoekstra et al., "Bioavailability of higher dose methotrexate comparing oral and subcutaneous administration in patients with rheumatoid arthritis," The Journal of Rheumatology, *J Rheumatol*, 31(4):645-648 (2004).

Hulot et al., "Dowe need a new P2Y12 receptor antagonist?," *European Heart Journal* 0:1-3 (2019).

Ibanez et al., "2017 ESC Guidelines for themanagement of acutemyocardial infarction in patients presenting with ST-segment elevation," *European Heart Journal*, 39:119-177 (2018).

Juif et al., "Clinical Pharmacology of the Reversible and Potent P2Y12 Receptor Antagonist ACT-246475 After Single Subcutaneous Administration in Healthy Male Subjects," *The Journal of Clinical Pharmacology*, 59(1): 123-130 (2019).

Kohn et al., "Prevalence of Acute Myocardial Infarction and Other Serious Diagnoses in Patients Presenting to An Urban Emergency Department with Chest Pain," *The Journal of Emergency Medicine*, 29(4):383-390 (2005).

Lee et al., "Self-Management of an Inferior ST-Segment Elevation Myocardial Infarction," *N Engl J Med*, 378(10):960-962 (2018).

Montalescot et al., "Effect of Pre-Hospital Ticagrelor During the First 24 h After Primary Percutaneous Coronary Intervention in Patients With ST-Segment Elevation Myocardial Infarction—The ATLANTIC-H24 Analysis," *JACC: Cardiovasular Interventions*, 9(7):646-56 (2016).

Montalescot et al., "Prehospital Ticagrelor in ST-Segment Elevation Myocardial Infarction," *N Engl J Med*, 371:1016-27 (2014).

Neumann et al., "2018 ESC/EACTS Guidelines onmyocardial Revascularization—The Task Force on myocardial revascularization of the European Society of Cardiology (ESC) and European Association for Cardio-Thoracic Surgery (EACTS)," *European Heart Journal*, 40:87-165 (2019).

O'Gara et al., "2013 ACCF/AHA Guideline for the Management of ST-Elevation Myocardial Infarction: Executive Summary," *Journal of the American College of Cardiology*, 61(4):485-510 (2013).

Roux et al., "Self-treatment for acute coronary syndrome: why not?," *Cardiopulse*, pp. 2144-2145 (2020).

Roux et al., "Experimental Carotid Thrombosis in the Guinea Pig," *Thrombosis and Haemostasis*, 71(2):252-256 (1994).

Schiff et al., "Head-to-head, randomised, crossover study of oral versus subcutaneous methotrexate in patients with rheumatoid arthritis: drug-exposure limitations of oral methotrexate at doses ≥15 mg may be overcome with subcutaneous administration," *Ann Rheum Dis*, 73:1549-1551 (2014).

Steg et al., "Effect of cangrelor on periprocedural outcomes in percutaneous coronary interventions: a pooled analysis of patient-level data," *Lancet*, 382:1981-92 (2013).

Storey et al., "Pharmacodynamics, pharmacokinetics, and safety of single-dose subcutaneous administration of selatogrel, a novel P2Y12 receptor antagonist, in patients with chronic coronary syndromes," *European Heart Journal*, 0:1-9 (2019).

Wang et al., "COVID-19: An Unintended Force for Medical Revolution?," *J Invasive Cardiol*, 32(4):E81-E82(2020).

Windecker et al., "2014 ESC/EACTS Guidelines onmyocardial Revascularization—The Task Force on Myocardial Revascularization of the European Society of Cardiology (ESC) and the European Association for Cardio-Thoracic Surgery (EACTS)," *European Heart Journal*, 35:2541-2619 (2014).

U.S. Appl. No. 11/912,545, filed Nov. 1, 2011, Caroff et al.
U.S. Appl. No. 12/090,816, filed Nov. 19, 2011, Binkert et al.
U.S. Appl. No. 12/445,352, filed Jan. 10, 2012, Caroff et al.
U.S. Appl. No. 12/447,039, filed Oct. 25, 2011, Caroff et al.
U.S. Appl. No. 12/745,358, filed Aug. 27, 2013, Caroff et al.
U.S. Appl. No. 12/936,661, filed Nov. 15, 2011, Caroff et al.
U.S. Appl. No. 12/936,664, filed Jun. 18, 2013, Caroff et al.
U.S. Appl. No. 13/263,089, filed Oct. 16, 2012, Caroff et al.
U.S. Appl. No. 13/265,493, filed Mar. 4, 2014, Caroff et al.
U.S. Appl. No. 16/335,973, filed Nov. 17, 2016, Chung et al.

Abele, S., "Pilot Plant Production of a $P2Y_{12}$-Antagonist Containing (R)-3- Phosphonoalanine," Abstract, *Actelion Pharmaceuticals Ltd.*, 250th ACS National Meeting, Process Chemistry: New Developments in Pharmaceutical Process Development (ORGN), 2015, 1 page.

Actelion Shareholder Information Brochure, "General Meeting of Shareholders: Proposed demerger of Actelion's drug discovery and early-stage clinical pipeline business," Mar. 15, 2017, 40 pages.

ACS Chemistry for Life, "$250^{th}$ Celebration American Chemical Society National Meeting & Exposition", Innovation from Discovery to Application, Boston, MA, Aug. 16-50, 2015, 2 pages.

Alexopoulos, D., "Randomized Assessment of Ticagrelor Versus Prasugrel Antiplatelet Effects in Patients with ST-Segment-Elevation Myocardial Infarction," *Circ Cardiovasc Interv*, 2012, vol. 5, pp. 797-804.

Amir, J. et al., "Treatment of Thrombotic Thrombocytopenic Purpura With Antiplatelet Drugs," *Blood*, 1973, vol. 42, No. 1, pp. 27-33.

Anderson, J.L. et al., "2011 ACCF/AHA Focused Update Incorporated Into the ACC/AHA 2007 Guidelines for the Management of Patients With Unstable Angina/Non—ST-Elevation Myocardial Infarction," *Circulation*, 2011, vol. 123, pp. e426-e579.

André, P., "$P2Y_{12}$ regulates platelet adhesion/activation, thrombus growth, and thrombus stability in injured arteries," *The Journal of Clinical Investigation*, 2003, vol. 112, No. 3, pp. 398-406.

André, P., "Thienopyridines, but Not Elinogrel, Result in Off-Target Effects at the Vessel Wall That Contribute to Bleeding," *The Journal of Pharmacology and Experimental Therapeautics*, 2011, vol. 338, No. 1, pp. 22-30.

Antithrombotic Trialists' Collaboration, "Collaborative metaanalysis of randomised trials of antiplatelet therapy for prevention of death, myocardial infarction, and stroke in high risk patients," *British Medical Journal*, 2002, vol. 324, pp. 71-86.

Antman, E.M. et al., "ACC/AHA Guidelines for the Management of Patients With ST-Elevation Myocardial Infarction—Executive Summary," *Circulation*, 2004, vol. 110, pp. 588-636.

Baldoni, D. et al., A New Reversible and Potent $P2Y_{12}$ Receptor Antagonist (ACT-246475): Tolerability, Pharmacokinetics, and Pharmacodynamics in a First-in-Man Trial, *Clinical Drug Investigation*, 2014, vol. 34, pp. 807-818.

(56) References Cited

OTHER PUBLICATIONS

Balduini, C.L. et al., "Platelet Aggregation in Platelet-Rich Plasma and Whole Blood in 120 Patients with Myeloproliferative Disorders," *American Journal of Clinical Pathology*, 1991, vol. 95, pp. 82-86.
Bartoli, G. et al., "Reactions of dianions of acyclic β-enamino ketones with electrophiles. 3. Nitriles: synthesis of pyridine and pyrimidine derivatives," *The Journal of Organic Chemistry*, 1992, vol. 57(22), pp. 6020-6025.
Becker, R.C. et al., "Platelet $P2Y_{12}$ receptor antagonist pharmacokinetics and pharmaco-dynamics: A foundation for distinguishing mechanisms of bleeding and anticipated risk for platelet-directed therapies," *Thrombosis and Haemostasis*, 2010, vol. 103, pp. 535-544.
Bellemain-Appaix, A. et al., "Association of Clopidogrel Pretreatment With Mortality, Cardiovascular Events, and Major Bleeding Among Patients Undergoing Percutaneous Coronary Intervention," *The Journal of the American Medical Association*, 2012, vol. 308, No. 23, pp. 2507-2516.
Bertrand, M.E. et al., "Randomized Multicenter Comparison of Conventional Anticoagulation Versus Antiplatelet Therapy in Unplanned and Elective Coronary Stenting," *Circulation*, 1998, vol. 98, pp. 1597-1603.
Blanger, G. et al., "New Approach to Aphidicolin and Total Asymmetric Synthesis of Unnatural (11R)-(—)-8-Epi-11-hydroxyaphidicolin by Tandem Transannular Diels—Alder/Aldol Reactions," *The Journal of Organic Chemistry*, 2000, vol. 65(21), pp. 7070-7074.
Brighton, T.A. et al., "Antiphospholipid antibodies and thrombosis," *Baillière's Clinical Haematology*, 1994, vol. 7, No. 3, pp. 541-557.
Cannon, C.P. et al., "Comparison of ticagrelor with clopidogrel in patients with a planned invasive strategy for acute coronary syndromes (PLATO): A randomised double-blind study," *The Lancet*, 2010, vol. 375, pp. 283-293.
Caprie Steering Committee, "A randomised, blinded, trial of clopidogrel versus aspirin in patients at risk of ischaemic events (CAPRIE)," *The Lancet*, 1996, vol. 348, pp. 1329-1339.
Caroff, E. et al., "4-((R)-2-{[6-((S)-3-Methoxypyrrolidin-1-yl)-2-phenylpyrimidine-4-carbonyl]amino}-3-phosphonopropionyl)piperazine-1-carboxylic Acid Butyl Ester (ACT-246475) and Its Prodrug (ACT-281959), a Novel $P2Y_{12}$ Receptor Antagonist with a Wider Therapeutic Window in the Rat Than Clopidogrel," *Journal of Medicinal Chemistry*, 2015, vol. 58, pp. 9133-9153.
Caroff, E. et al., "Optimization of 2-phenyl-pyrimidine-4-carboxamides towards potent, orally bioavailable and selective $P2Y_{12}$ antagonists for inhibition of platelet aggregation," *Bioorganic & Medicinal Chemistry Letters*, 2014, vol. 24, pp. 4323-4331.
Cattaneo, M., "The platelet $P2Y_{12}$ receptor for adenosine diphosphate: congenital and drug-induced defects," *Blood*, 2011, vol. 117, No. 7, pp. 2102-2112.
Charette, A.B. et al., "Enantioselective Cyclopropanation of Allylic Alcohols with Dioxaborolane Ligands: Scope and Synthetic Applications," *Journal of the American Chemical Society*, 1998, vol. 120(46), pp. 11943-11952.
Coller, B.S., "Historical Perspective and Future Directions in Platelet Research," *Journal of Thrombosis and Haemostasis*, 2011, vol. 9(Suppl 1), 38 pages.
Collins, C.E. et al., "Review article: platelets in inflammatory bowel disease—pathogenetic role and therapeutic implications," *Aliment Pharmacol Ther*, 1997, vol. 11, pp. 237-247.
Davì, G. et al., "Platelet Activation and Atherothrombosis," *The New England Journal of Medicine*, 2007, vol. 357(24), pp. 2482-2494.
Davies, M.J. et al., "Intramyocardial platelet aggregation in patients with unstable angina suffering sudden ischemic cardiac death," *Circulation*, 1986, vol. 73, No. 3, pp. 418-427.
Dunning, A.J. et al., "Feasibility of self-administration of lidocaine and atropine in the prehospital phase of acute myocardial infarction," *The Netherlands Journal of Medicine*, 1973, vol. 16(4-5), pp. 178-188.

Felfernig-Boehm, D. et al., "Early Detection of Preeclampsia by Determination of Platelet Aggregability," *Thrombosis Research*, 2000, vol. 98, pp. 139-146.
Feoktistov, I. et al., "Adenosine $A_{2B}$ Receptors," *Pharmacological Reviews*, 1997, vol. 49, No. 4, pp. 381-402.
Fox, K.A.A. et al., "Benefits and Risks of the Combination of Clopidogrel and Aspirin in Patients Undergoing Surgical Revascularization for Non-ST-Elevation Acute Coronary Syndrome: The Clopidogrel in Unstable angina to prevent Recurrent ischemic Events (CURE) Trial," *Circulation*, 2004, vol. 110, pp. 1202-1208.
Franchi, F. et al., "Novel antiplatelet agents in acute coronary syndrome," *Nat. Rev. Cardiol.*, 2015, vol. 12, pp. 30-47.
Halushka, P.V. et al., "Protective Effects of Aspirin in Endotoxic Shock," *The Journal of Pharmacology and Experimental Therapeutics*, 1981, vol. 218, No. 2, pp. 464-469.
Herrmann, H.C. et al., "Benefit of Facilitated Percutaneous Coronary Intervention in High-Risk ST-Segment Elevation Myocardial Infarction Patients Presenting to Nonpercutaneous Coronary Intervention Hospitals," *JACC: Cardiovascular Interventions*, 2009, vol. 2, No. 10, pp. 917-924.
Hovens, M.M.C. et al., "Aspirin in the prevention and treatment of venous thromboembolism," *Journal of Thrombosis and Haemostasis*, 2006, vol. 4, pp. 1470-1475.
Husted, S. et al., "Pharmacodynamics, pharmacokinetics, and safety of the oral reversible $P2Y_{12}$ antagonist AZD6140 with aspirin in patients with atherosclerosis: a double-blind comparison to clopidogrel with aspirin," *European Heart Journal*, 2006, vol. 27, pp. 1038-1047.
Idorsia Pharmaceuticals Ltd., "Single-ascending Oral Dose Study to Investigate the Safety, Tolerability, Pharmacokinetics, and Pharmacodynamics of ACT-281959 / ACT-246475 in Healthy Male Subjects," *U.S. National Library of Medicine*, ClinicalTrials.gov Identifier: NCT01954615, 2013, 8 pages.
Idorsia Pharmaceuticals Ltd., "A Medical Research Study to Evaluate the Effects of ACT-246475 in Adults With Coronary Artery Disease," *U.S. National Library of Medicine*, ClinicalTrials.gov Identifier: NCT03384966, 2017, 6 pages.
Idorsia Pharmaceuticals Ltd., "A Study to Investigate the Interaction Between ACT-246475 and Clopidogrel, Prasugrel, and Ticagrelor in Healthy Subjects," *U.S. National Library of Medicine*, ClinicalTrials.gov Identifier: NCT03430661, 2018, 8 pages.
Idorsia Pharmaceuticals Ltd., "A Study to Evaluate ACT-246475 Fate in Healthy Male Subjects," *U.S. National Library of Medicine*, ClinicalTrials.gov Identifier: NCT03593278, 2018, 4 pages.
Idorsia Pharmaceuticals Ltd., "A Medical Research Study to Evaluate the Effects of ACT-246475 in Adults With Heart Attack," *U.S. National Library of Medicine*, ClinicalTrials.gov Identifier: NCT03487445, 2018, 4 pages.
Idorsia Pharmaceuticals Ltd., "A Study to Investigate the Effect of Rifampicin on the Uptake and Breakdown of ACT-246475 in Healthy Subjects," *U.S. National Library of Medicine*, ClinicalTrials.gov Identifier: NCT03814200, 2019, 5 pages.
Idorsia Pharmaceuticals Ltd., "A multi-center, double-blind, randomized, placebo-controlled study to assess the pharmacodynamics, pharmacokinetics, tolerability, and safety of a single subcutaneous injection of ACT-246475 in adults with stable coronary artery disease," *EU Clinical Trials Register*, EudraCT No. 2017-003332-36, 2017, 5 pages.
Jagroop, I.A. et al., "The effect of clopidogrel, aspirin and both antiplatelet drugs on platelet function in patients with peripheral arterial disease," *Platelets*, 2004, vol. 15, No. 2, pp. 117-125.
Jneid, H. et al., "2012 ACCF/AHA Focused Update of the Guideline for the Management of Patients With Unstable Angina/Non-ST-Elevation Myocardial Infarction (Updating the 2007 Guideline and Replacing the 2011 Focused Update)," *Journal of the American College of Cardiology*, 2012, vol. 60, No. 7, pp. 645-681.
Kharbanda, R.K. et al., "Prevention of Inflammation-Induced Endothelial Dysfunction," *Circulation*, 2002, vol. 105, pp. 2600-2604.
Kralev, S., "The 'chest pain kit' study: A 'pill in the pocket' concept to improve the pre-hospital therapy of acute coronary syndrome," *Cardiology Journal*, 2010, vol. 17, No. 5, pp. 528-531.

(56) References Cited

OTHER PUBLICATIONS

Liu, F. et al., "P2Y$_{12}$ receptor inhibitors for secondary prevention of ischemic stroke," *Expert Opinion on Pharmacotherapy*, 2015, vol. 16, No. 8, pp. 1149-1165.

Lupi, A. et al., "Pre-hospital ticagrelor in patients with ST-segment elevation myocardial infarction with long transport time to primary PCI facility," *Cardiovascular Revascularization Medicine*, 2016, vol. 17, pp. 528-534.

Matsagas, M. et al., "The Effect of a Loading Dose (300 mg) of Clopidogrel on Platelet Function in Patients with Peripheral Arterial Disease," *Clin Appl Thromboses/Hemostasis*, 2003, vol. 9, No. 2, pp. 115-120.

Megalopoulos, A. et al., "Recurrent arterial thromboses in a woman with heparin induced thrombocytopenia, successfully managed with iloprost followed by clopidogrel. An alternative therapeutic option for heparin induced thrombocytopenia type II syndrome," *International Angiology*, 2006, vol. 25, No. 1, pp. 84-89.

Mehta, S.R. et al., "Effects of pretreatment with clopidogrel and aspirin followed by long-term therapy in patients undergoing percutaneous coronary intervention: the PCI-CURE study," *The Lancet*, 2001, vol. 358, pp. 527-533.

Michelson, A.D., "Methods for the Measurement of Platelet Function," *The American Journal of Cardiology*, 2009, vol. 103(Suppl), pp. 20A-26A.

Montalescot, G. et al., "Pretreatment with Prasugrel in Non-ST-Segment Elevation Acute Coronary Syndromes," *The New England Journal of Medicine*, 2013, vol. 369, No. 11, pp. 999-1010.

Montalescot, G. et al., A.W., "Prehospital Ticagrelor in ST-Segment Elevation Myocardial Infarction," *The New England Journal of Medicine*, 2014, vol. 371, No. 24, pp. 2337-2339.

Norgard, N.B., "Cangrelor: a novel P2Y$_{12}$ receptor antagonist," *Expert Opinion on Investigational Drugs*, 2009, vol. 18, No. 8, pp. 1219-1230.

Notice of Allowance dated Jun. 27, 2011, for U.S. Appl. No. 12/936,661, p. 1.

Office Action dated Aug. 31, 2012, for U.S. Appl. No. 12/936,664, p. 1.

Office Action dated Jan. 19, 2011, for U.S. Appl. No. 12/445,352, p. 1.

Office Action dated Jan. 21, 2011, for U.S. Appl. No. 12/936,661, p. 1.

Office Action dated Oct. 28, 2010, for U.S. Appl. No. 11/912,545, p. 1.

O'Gara, P.T. et al., "2013 ACCF/AHA Guideline for the Management of ST-Elevation Myocardial Infarction," *Circulation*, 2013, vol. 127, pp. e362-e425.

Oliphant, C.S. et al., "Clopidogrel Response Variability: Review of the Literature and Practical Considerations," *Journal of Pharmacy Practice*, 2016, vol. 29, No. 1, pp. 26-34.

Parlow, J.J. et al., "Piperazinyl-glutamate-pyridines as potent orally bioavailable P2Y$_{12}$ antagonists for inhibition of platelet aggregation," *Bioorganic & Medificnal Chemistry Letters*, 2009, vol. 19, pp. 4657-4663.

Parlow, J.J. et al., "Piperazinyl-glutamate-pyrimidines as potent P2Y$_{12}$ antagonists for inhibition of platelet aggregation," *Bioorganic & Medicinal Chemistry Letters*, 2009, vol. 19, pp. 6148-6156.

Parlow, J.J. et al., "Piperazinyl Glutamate Pyridines as Potent Orally Bioavailable P2Y$_{12}$ Antagonists for Inhibition of Platelet Aggregation," *Journal of Medicinal Chemistry*, 2010, vol. 53, pp. 2010-2037.

Parodi, G. et al., "Comparison of Prasugrel and Ticagrelor Loading Doses in ST-Segment Elevation Myocardial Infarction Patients," *Journal of the American College of Cardiology*, 2013, vol. 61, No. 15, pp. 1601-1606.

Redfors, B. et al., "The ATLANTIC Trial Does Not Support the Safety of Prehospital Ticagrelor Treatment for Patients with ST-Elevation Myocardial Infarction," *International Journal of Cardiology*, 2015, vol. 190, pp. 157-158.

Payne, D.A. et al., "Beneficial Effects of Clopidogrel Combined With Aspirin in Reducing Cerebral Emboli in Patients Undergoing Carotid Endarterectomy," *Circulation*, 2004, vol. 109, pp. 1476-1481.

Remington, The Science and Practice of Pharmacy, 21$^{st}$ Edition, 2005, Part 5, Pharmaceutical Manufacturing, 5 pages.

Rey, M. et al., "The reversible P2Y$_{12}$ antagonist ACT-246475 causes significantly less blood loss than ticagrelor at equivalent antithrombotic efficacy in rat," *Pharmacology Research & Perspectives*, 2017, vol. 5, No. 5, pp. 1-11 (e00338).

Siller-Matula, J.M., "Pharmacokinetic, Pharmacodynamic and Clinical Profile of Novel Antiplatelet Drugs Targeting Vascular Diseases," *British Journal of Pharmacology*, 2010, vol. 159, pp. 502-517.

Stahl, P.H. et al., "Handbook of Pharmaceutical Salts. Properties, Selection and Use" *International Union of Pure and Applied Chemistry (IUPAC)*, 2008, pp. 330-350.

Sabatine, M.S. et al., "Effect of Clopidogrel Pretreatment Before Percutaneous Coronary Intervention in Patients With ST-Elevation Myocardial Infarction Treated With Fibrinolytics," *The Journal of the American Medical Association*, 2005, vol. 294, No. 10, pp. 1224-1232.

Serebruany, V. et al., "Significant excess of early deaths after prehospital ticagrelor: The ATLANTIC trial challenge," *Thrombosis and Haemostasis*, 2015, vol. 114, pp. 7-8.

Shao, B. et al., "Phenoxyphenyl Pyridines as Novel State-Dependent, High-Potency Sodium Channel Inhibitors," *Journal of Medicinal Chemistry*, 2004, vol. 47, No. 17, pp. 4277-4285.

Sheppard, G.S. et al., "Discovery and Optimization of Anthranilic Acid Sulfonamides as Inhibitors of Methionine Aminopeptidase-2: A Structural Basis for the Reduction of Albumin Binding," *Journal of Medicinal Chemistry*, 2006, vol. 49, No. 13, pp. 3832-3849.

Stathakis, N.E. et al., "Platelet Dysfunction in Essential Thrombocythaemia," *Annals of Clinical Research*, 1974, vol. 6, pp. 198-202.

Storey, R.F. et al., "Inhibitory Effects of Ticagrelor Compared With Clopidogrel on Platelet Function in Patients With Acute Coronary Syndromes," *Journal of the American College of Cardiology*, 2010, vol. 56, No. 18, pp. 1456-1462.

Ten Berg, J.M. et al., "Effect of Early, Pre-Hospital Initiation of High Bolus Dose Tirofiban in Patients With ST-Segment Elevation Myocardial Infarction on Short- and Long-Term Clinical Outcome," *Journal of the American College of Cardiology*, 2010, vol. 55, No. 22, pp. 2446-2455.

Tfelt-Hansen, P., "Parenteral vs. oral sumatriptan and naratriptan: plasma levels and efficacy in migraine. A comment," *J Headache Pain*, 2007, vol. 8, pp. 273-276.

Thomas, M.R. et al., "The future of P2Y receptor antagonists," *Platelets*, 2015, vol. 26, No. 5, pp. 392-398.

Thorsen, C.A. et al., "The Treatment of the Hemolytic-Uremic Syndrome with Inhibitors of Platelet Function," *The American Journal of Medicine*, 1979, vol. 66, pp. 711-716.

Triadou, P. et al., "Platelet function in sickle cell disease during steady state," *Nouvelle Revue Francaise Hematologic*, 1990, vol. 32, pp. 137-142.

Turpie, A.G.G. et al., "Review of enoxaparin and its clinical applications in venous and arterial thromboembolism," *Expert Opinion Pharmacotherapy*, 2002, vol. 3, No. 5, pp. 575-598.

University of Perugia, "Aspirin for the Prevention of Recurrent Venous Thromboembolism," *U.S. National Library of Medicine*, ClinicalTrials.gov Identifier: NCT00222677, 2005, 6 pages.

Valgimigli, M. et al., "Prasugrel Versus Tirofiban Bolus With or Without Short Post-Bolus Infusion With or Without Concomitant Prasugrel Administration in Patients With Myocardial Infarction Undergoing Coronary Stenting," *JACC: Cardiovascular Interventions*, 2012, vol. 5, No. 3, pp. 268-277.

Van Giezen, J.J.J. et al., "Comparison of ticagrelor and thienopyridine P2Y$_{12}$ binding characteristics and antithrombotic and bleeding effects in rat and dog models of thrombosis/hemostasis," *Thrombosis Research*, 2009, vol. 124, pp. 565-571.

Van'T Hof, A.W.J. et al., "Prehospital initiation of tirofiban in patients with ST-elevation myocardial infarction undergoing pri-

(56) References Cited

OTHER PUBLICATIONS mary angioplasty (On-TIME 2): a multicentre, double-blind, randomised controlled trial," *The Lancet,* 2008, vol. 372, pp. 537-546.

Wallentin, L. et al., "Ticagrelor versus Clopidogrel in Patients with Acute Coronary Syndromes," *The New England Journal of Medicine,* 2009, vol. 361, No. 11, pp. 1045-1057.

Wallentin, L., "$P2Y_{12}$ inhibitors: differences in properties and mechanisms of action and potential consequences for clinical use," *European Heart Journal,* 2009, vol. 30, pp. 1964-1977.

Wiviott, S.D. et al., "Prasugrel Compared With High Loading- and Maintenance-Dose Clopidogrel in Patients With Planned Percutaneous Coronary Intervention," *Circulation,* 2007, vol. 116, pp. 2923-2932.

Wiviott, S.D. et al., "Clinical evidence for oral antiplatelet therapy in acute coronary syndromes," *Lancet,* 2015, vol. 386, pp. 292-302.

Wouters, J. et al., Pharmaceutical Salts and Co-crystals, *RSC Drug Discovery Series No. 16,* 2012, Chapters 7-14, 10 pages.

Yao, S.K. et al., "Clopidogrel is more effective than aspirin as adjuvant treatment to prevent reocclusion after thrombolysis," *The American Journal of Physiology,* 1994, vol. 267, pp. H488-H493.

Zeymer, U. et al., "Efficacy and safety of a high loading dose of clopidigrel administered prehospitally to improve primary percutaneous coronary intervention in acute myocardial infarction: the randomized CIPAMI trial," *Clin Res Cardiol,* 2012, vol. 101, pp. 305-312.

Tang et al. "Impact of New Oral or Intravenous P2Y12 Inhibitors and Clopidogrel on Major Ischemic and Bleeding Events in Patients with Coronary Artery Disease: A Meta-Analysis of Randomized Trials." *Atherosclerosis* 233.2 (2014): 568-578.

Wells et al. "Expanding Eligibility for Outpatient Treatment of Deep Venous Thrombosis and Pulmonary Embolism With Low-Molecular-Weight Heparin: A Comparison of Patient Self-Injection With Homecare Injection." *Arch Intern Med.* 1998; 158(16):1809-1812.

\* cited by examiner

Fig. 1   AF488-Fibrinogen binding intensity after subcutaneous administration of Compound 1 hydrochlorid (0.2 mg/kg) in male Balb/c mice
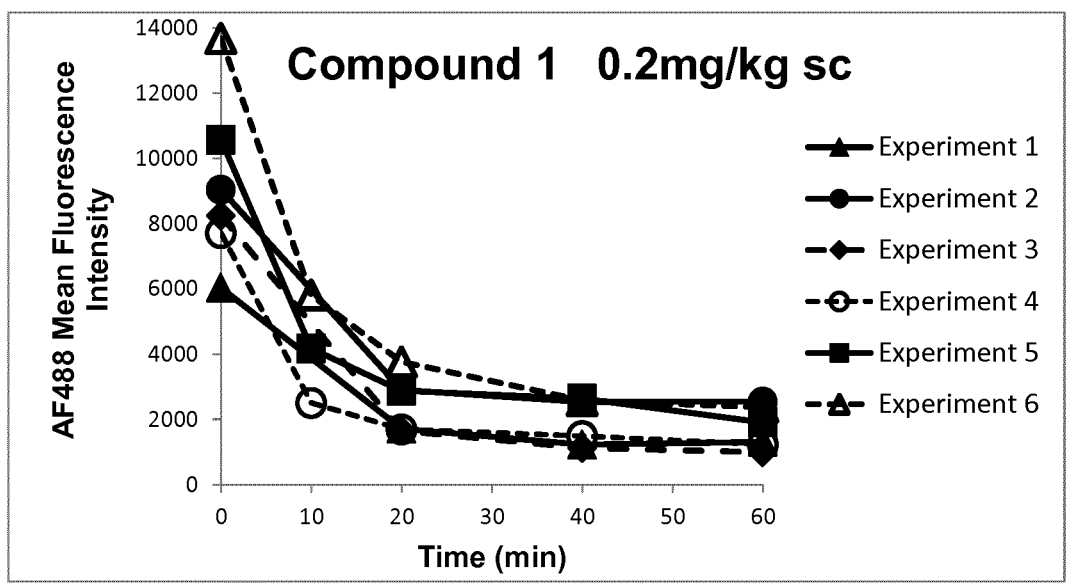

Fig. 2   AF488-Fibrinogen binding intensity after subcutaneous administration of Ticagrelor (1.0 mg/kg) in male Balb/c mice
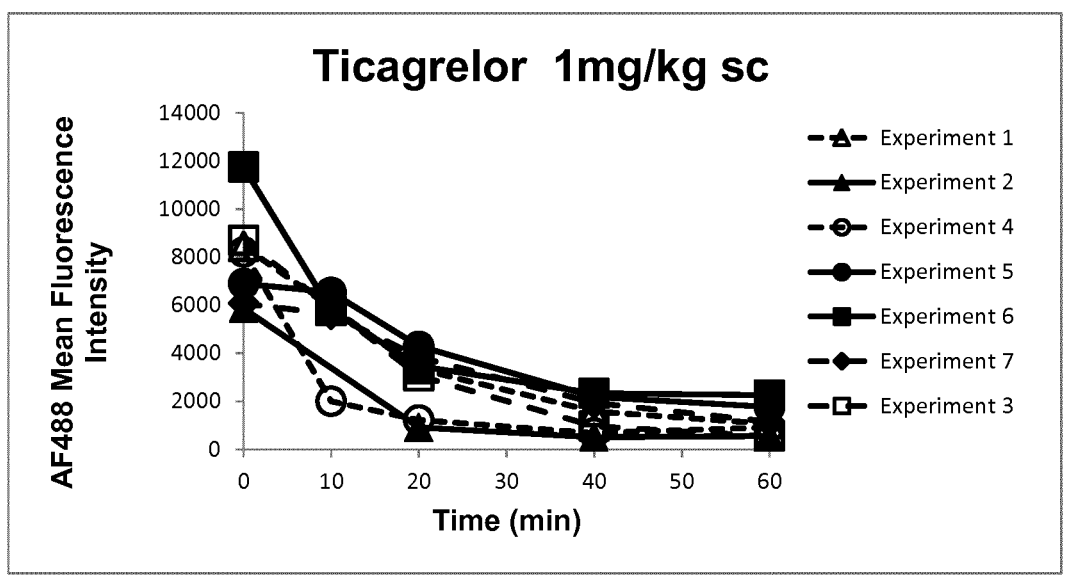

Fig. 3  AF488-Fibrinogen binding intensity after subcutaneous administration of Elinogrel (30 mg/kg) in male Balb/c mice
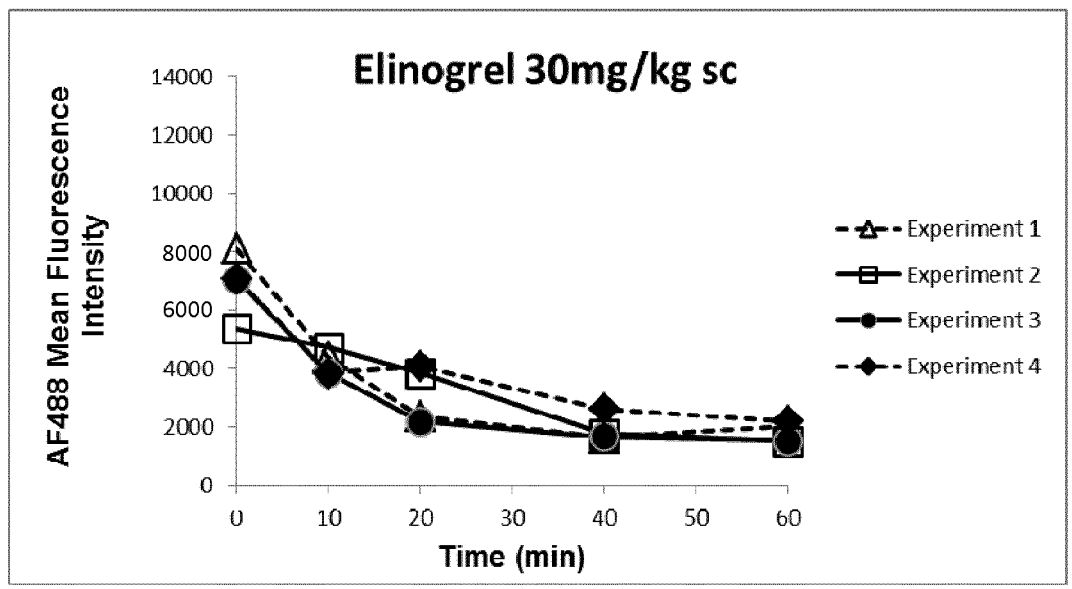

Fig. 4    AF488-Fibrinogen binding intensity after subcutaneous administration of Cangrelor (0.2 mg/kg) in male Balb/c mice
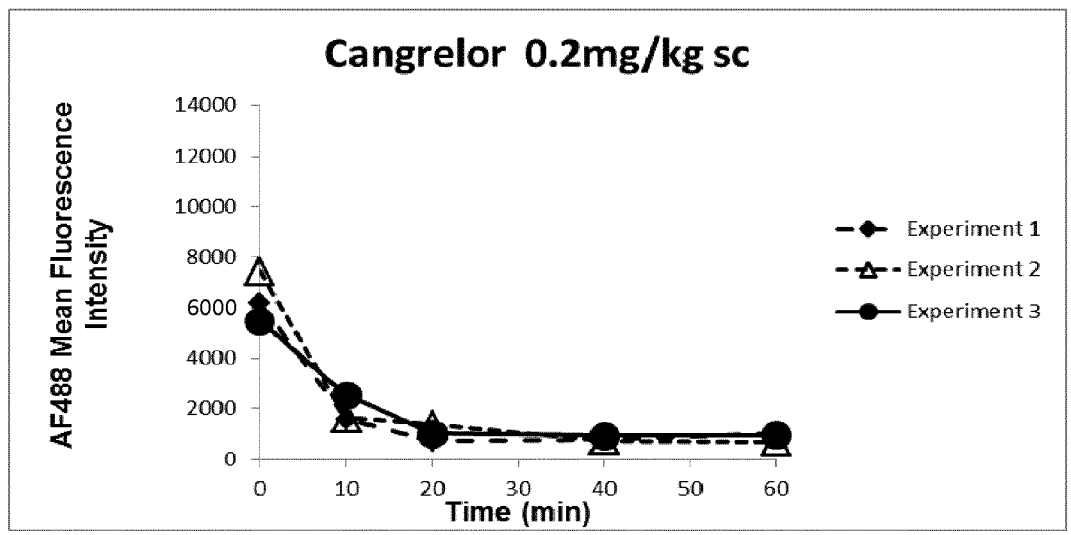

SUBCUTANEOUS ADMINISTRATION OF A P2Y$_{12}$ RECEPTOR ANTAGONIST

FIELD OF THE INVENTION

The present invention relates to a P2Y$_{12}$ receptor antagonist selected from the group consisting of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester (hereinafter also referred to as "Compound 1"), (1S,2S,3R,5S)-3-[7-[(1R,2S)-2-(3,4-difluorophenyl)cyclopropylamino]-5-(propylthio)-3H-[1,2,3]triazolo[4,5-d]pyrimidin-3-yl]-5-(2-hydroxyethoxy)cyclopentane-1,2-diol (hereinafter also referred to as "Ticagrelor"), and (1 S,2R,3S,4R)-4-[7-[(1R,2S)-2-(3,4-difluorophenyl)cyclopropylamino]-5-(propylthio)-3H-[1,2,3]triazolo[4,5-d]pyrimidin-3-yl]cyclopentane-1,2,3-triol (hereinafter also referred to as "Ticagrelor-M"), or a pharmaceutically acceptable salt thereof, for use as a medicament by subcutaneous or intradermal administration.

BACKGROUND OF THE INVENTION

When vascular integrity is compromised, circulating platelets adhere to the damaged vessel wall and aggregate, forming a plug that seals off the site of injury to prevent blood loss. Autopsy studies demonstrated that rupture of atherosclerotic plaques can lead to uncontrolled platelet thrombus formation and vessel occlusion (Davies M J et al. (1986) Circulation 73:418-427). Inhibition of platelet aggregation is recognized as an effective strategy for prevention of atherothrombotic events in patients with atherosclerotic disease in the coronary, peripheral, and cerebrovascular circulation (Davi G et al. (2007) N Engl J Med 357:2482-2494).

The ADP receptors P2Y$_1$ and P2Y$_{12}$ play a critical role in platelet activation and aggregation (Andre P et al. (2003) J Clin Invest 112:398-406). Inhibition of the P2Y$_{12}$ receptor is a validated concept for prevention of major adverse cardiovascular events in patients with acute coronary syndromes (ACS) as demonstrated by the thienopyridines ticlopidine, clopidogrel and prasugrel (Franchi F et al. (2015) Nat Rev Cardiol 12:30-47). These drugs following metabolic activation irreversibly block the P2Y$_{12}$ receptor and platelet function (Antman E M et al. (2004) Circulation 110:588-636; Anderson J L et al. (2011) Circulation 123:e426-579) resulting in increased efficacy and increased bleeding (Wiviott S D et al. (2007) Circulation 116:2923-2932). In studies using P2Y$_{12}$ knockout mice it was shown that clopidogrel and prasugrel caused more blood loss following tail transection as compared with vehicle indicating that the increased blood loss may be due to off-target effects of the thienopyridines (Andre P et al. (2011) J Pharmacol Exp Ther 338:22-30). Preclinical studies with the direct-acting and reversibly binding P2Y$_{12}$ antagonist ticagrelor demonstrated a wider therapeutic window in rat and dog thrombosis models as compared with clopidogrel (van Giezen J J et al. (2009) Thromb Res 124:565-571; Becker R C et al. (2010) Thromb Haemost 103:535-544). It was argued that the reversibility of the binding of ticagrelor to P2Y$_{12}$ might account for this difference. In patients, ticagrelor achieved a higher extent of inhibition of ADP-induced platelet aggregation than clopidogrel (Husted S et al. (2006) Eur Heart J 27:1038-1047; Cannon C P et al. (2010) Lancet 375:283-293) and in the pivotal phase III trial (PLATO) in post acute coronary syndrome patients, ticagrelor showed superior efficacy and no significant difference in the risk of major bleeding events to clopidogrel. However, a significant increase in fatal intracranial bleedings and in major or minor bleedings according to the study criteria was reported for ticagrelor (Wallentin L et al. (2009) N Engl J Med 361:1045-1057).

Several studies confirmed the benefit of earlier administration of inhibitors of platelet function, for example glycoprotein IIb/IIIa inhibitors in patients with ST elevation myocardial infarction (STEMI), especially in those presenting very soon after symptom onset (Van't Hof A W et al. (2008) Lancet 372:537-546; Herrmann H C et al. (2009) JACC Cardiovasc Interv 2:917-924; ten Berg J M et al. (2010) J Am Coil Cardiol 55:2446-2455). Furthermore, various studies and meta-analyses suggested that pretreatment with clopidogrel in patients with STEMI could reduce the rate of ischemic events without excess bleeding (Sabatine M S et al. (2005) JAMA 294:1224-1232; Bellemain-Appaix A et al. (2012) JAMA 308:2507-2516; Zeymer U et al. (2012) Clin Res Cardiol 101:305-312). However, the effectiveness of clopidogrel is limited by its slow onset of action and the variable response (Oliphant C S et al. (2016) J Pharm Pract 29:26-34). The oral P2Y$_{12}$-receptor antagonists ticagrelor and prasugrel were reported to inhibit platelet function in less than 1 hour (Storey R F et al. (2010) J Am Coil Cardiol 56:1456-1462; Wiviott S D et al. (2007) Circulation 116:2923-2932). However, contradictory studies suggested that the full effect of prasugrel or ticagrelor on platelet function may take several hours in patients with STEMI (Alexopoulos D et al. (2012) Circ Cardiovasc Interv 5:797-804; Valgimigli M et al. (2012) JACC Cardiovasc Interv 5:268-277; Parodi G et al. (2013) J Am Coil Cardiol 61:1601-1606; Montalescot G et al. (2014) N Engl J Med 371:2339). Indeed, in the ATLANTIC clinical trial (Montalescot G et al. (2013) N Engl J Med 369:999-1010) it was found that the two coprimary end points did not differ significantly between a group of patients with ongoing STEMI that has received an early prehospital treatment (in the ambulance) of oral Ticagrelor and a group that has received the treatment only later in the hospital (in the catheterization laboratory). The two coprimary endpoints were (i) the proportion of patients who did not have a 70% or greater resolution of ST-segment elevation before percutaneous coronary intervention (PCI) and (ii) the proportion of patients who did not have Thrombolysis in Myocardial Infarction flow grade 3 in the infarct-related artery at initial angiography. Montalescot et al. stated that besides an extremely short time to PCI in this study "another potential limitation is related to the delayed absorption of orally administered P2Y$_{12}$ receptor antagonists" and that the "onset of action may have been delayed further by morphine co-administration in half of the study population". There is thus a strong need for a treatment option resulting in a fast and high inhibition of platelet aggregation in patients with, for instance, acute coronary syndromes, wherein the inhibition of platelet aggregation is achieved as early as possible after cardiac symptom onset. It is surprisingly found that this need can be fulfilled if a P2Y$_{12}$ receptor antagonist (especially Compound 1) is administered to a patient subcutaneously, especially if the P2Y$_{12}$ receptor antagonist is administered by the patient or a relative even before arrival of ambulance health care provider. To be useful in such a subcutaneous administration form the P2Y$_{12}$ receptor antagonist needs to have a specific combination of physicochemical and pharmacological properties as is the case for Compound 1 in contrast to most of the known and approved P2Y$_{12}$ receptor antagonists. Compound 1 is a direct-acting and reversible P2Y$_{12}$ antagonist (Caroff E et al. (2015) J Med Chem 58:9133-9153) and thus requires no metabolic activation that typically results in a slow onset of action and a significant dependency of pharmacodynamics from metabolism of each individual patient. No bleeding events were observed in a clinical phase I study after oral administration of Compound 1 or its prodrug (Baldoni D et al. (2014) Clin Drug Investig 34(11):807-818); and in a $FeCl_3$ rat thrombosis model, Compound 1 was shown to have a significantly wider therapeutic window even than Ticagrelor (Rey M et al. (2017) Pharma Res Per 5(5):e00338 (doi: 10.1002/prp2.338)). Compound 1 is very potent and highly soluble in aqueous media (75 mg/mL for the lyophilized disodium salt of Compound 1, reconstituted in water, pH=8.4) and is therefore compatible with the limited volume that can be administered subcutaneously in a typical bolus-injection. Results from a clinical phase I study in healthy volunteers indicate that the pharmacokinetic and pharmacodynamic properties of Compound 1 are suitable for a subcutaneous administration. For instance, at doses ≥8 mg Compound 1, the peak % IPA (inhibition of platelet aggregation) exceeded 85% in less than 15 min.

DESCRIPTION OF THE FIGURES

FIG. 1 shows the time dependency of the AF488-Fibrinogen binding intensity after subcutaneous administration of Compound 1 hydrochlorid (0.2 mg/kg) in male Balb/c mice.

FIG. 2 shows the time dependency of the AF488-Fibrinogen binding intensity after subcutaneous administration of Ticagrelor (1.0 mg/kg) in male Balb/c mice.

FIG. 3 shows the time dependency of the AF488-Fibrinogen binding intensity after subcutaneous administration of Elinogrel (30 mg/kg) in male Balb/c mice.

FIG. 4 shows the time dependency of the AF488-Fibrinogen binding intensity after subcutaneous administration of Cangrelor (0.2 mg/kg) in male Balb/c mice.

DETAILED DESCRIPTION OF THE INVENTION

Various embodiments of the invention are presented hereafter:

1) A first embodiment of the invention relates to a $P2Y_{12}$ receptor antagonist, or a pharmaceutically acceptable salt thereof, for use in the prevention or treatment (preferably treatment) of a disease, wherein the disease is selected from acute arterial thromboses and acute venous thromboses; wherein the $P2Y_{12}$ receptor antagonist is selected from the group consisting of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester (Compound 1), (1 S,2S,3R,5S)-3-[7-[(1R,2S)-2-(3,4-difluorophenyl)cyclopropylamino]-5-(propylthio)-3H-[1,2,3]triazolo[4,5-d]pyrimidin-3-yl]-5-(2-hydroxyethoxy)cyclopentane-1,2-diol (Ticagrelor), and (1S,2R,3S,4R)-4-[7-[(1R,2S)-2-(3,4-difluorophenyl)cyclopropylamino]-5-(propylthio)-3H-[1,2,3]triazolo[4,5-d]pyrimidin-3-yl] cyclopentane-1,2,3-triol (Ticagrelor-M); and wherein the $P2Y_{12}$ receptor antagonist is administered and/or is to be administered to a patient by intradermal or subcutaneous administration.

2) A further embodiment of the invention relates to a $P2Y_{12}$ receptor antagonist (notably Compound 1), or a pharmaceutically acceptable salt thereof, for use according to embodiment 1), wherein the disease is selected from acute arterial thromboses.

3) A further embodiment of the invention relates to a $P2Y_{12}$ receptor antagonist (notably Compound 1), or a pharmaceutically acceptable salt thereof, for use according to embodiment 1), wherein the disease is selected from acute coronary syndromes, myocardial infarction, peripheral ischaemia, amaurosis, sudden cardiac death, ischaemic stroke and transient ischaemic attack.

4) A further embodiment of the invention relates to a $P2Y_{12}$ receptor antagonist (notably Compound 1), or a pharmaceutically acceptable salt thereof, for use according to embodiment 1), wherein the disease is selected from acute coronary syndromes, peripheral ischaemia, amaurosis, ischaemic stroke and transient ischaemic attack.

5) A further embodiment of the invention relates to a $P2Y_{12}$ receptor antagonist (notably Compound 1), or a pharmaceutically acceptable salt thereof, for use according to embodiment 1), wherein the disease is acute coronary syndromes.

6) A further embodiment of the invention relates to a $P2Y_{12}$ receptor antagonist (notably Compound 1), or a pharmaceutically acceptable salt thereof, for use according to embodiment 1), wherein the disease is myocardial infarction.

7) A further embodiment of the invention relates to a $P2Y_{12}$ receptor antagonist (notably Compound 1), or a pharmaceutically acceptable salt thereof, for use according to embodiment 1), wherein the disease is peripheral ischaemia.

8) A further embodiment of the invention relates to a $P2Y_{12}$ receptor antagonist (notably Compound 1), or a pharmaceutically acceptable salt thereof, for use according to embodiment 1), wherein the disease is amaurosis.

9) A further embodiment of the invention relates to a $P2Y_{12}$ receptor antagonist (notably Compound 1), or a pharmaceutically acceptable salt thereof, for use according to embodiment 1), wherein the disease is sudden cardiac death.

10) A further embodiment of the invention relates to a $P2Y_{12}$ receptor antagonist (notably Compound 1), or a pharmaceutically acceptable salt thereof, for use according to embodiment 1), wherein the disease is selected from ischaemic stroke and transient ischaemic attack.

11) A further embodiment of the invention relates to a $P2Y_{12}$ receptor antagonist (notably Compound 1), or a pharmaceutically acceptable salt thereof, for use according to any one of embodiments 1) to 10), wherein the $P2Y_{12}$ receptor antagonist is administered and/or is to be administered prior to hospitalization.

12) A further embodiment of the invention relates to a $P2Y_{12}$ receptor antagonist (notably Compound 1), or a pharmaceutically acceptable salt thereof, for use according to embodiment 11), wherein the $P2Y_{12}$ receptor antagonist is administered and/or is to be administered by patient self-administration.

13) A further embodiment of the invention relates to a $P2Y_{12}$ receptor antagonist (notably Compound 1), or a pharmaceutically acceptable salt thereof, for use according to embodiment 11), wherein the $P2Y_{12}$ receptor antagonist is administered and/or is to be administered by a health care professional.

14) A further embodiment of the invention relates to a $P2Y_{12}$ receptor antagonist, or a pharmaceutically acceptable salt thereof, for use in the emergency treatment of suspected acute coronary syndromes (ACS) by patient self-administration prior to hospitalization; wherein the $P2Y_{12}$ receptor antagonist is selected from the group consisting of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester (Compound 1), (1S,2S,3R,5S)-3-[7-[(1R,2S)-2-(3,4-difluorophenyl)cyclopropylamino]-5-(propylthio)-3H-[1,2,3]triazolo[4,5-d]pyrimidin-3-yl]-5-(2-hydroxyethoxy)cyclopentane-1,2-diol (Ticagrelor) and (1 S,2R,3S,4R)-4-[7-[(1R,2S)-2-(3,4-difluorophenyl)

cyclopropylamino]-5-(propylthio)-3H-[1,2,3]triazolo[4,5-d]pyrimidin-3-yl]cyclopentane-1,2,3-triol (Ticagrelor-M); and wherein the $P2Y_{12}$ receptor antagonist is administered and/or is to be administered to a patient by intradermal or subcutaneous administration.

15) A further embodiment of the invention relates to a $P2Y_{12}$ receptor antagonist (notably Compound 1), or a pharmaceutically acceptable salt thereof, for use according to any one of embodiments 1) to 14), wherein the $P2Y_{12}$ receptor antagonist is administered and/or is to be administered to a patient by subcutaneous administration.

16) A further embodiment of the invention relates to a $P2Y_{12}$ receptor antagonist (notably Compound 1), or a pharmaceutically acceptable salt thereof, for use according to any one of embodiments 1) to 15), wherein the $P2Y_{12}$ receptor antagonist is administered and/or is to be administered by use of an auto-injector device.

17) A further embodiment of the invention relates to a $P2Y_{12}$ receptor antagonist (notably Compound 1), or a pharmaceutically acceptable salt thereof, for use according to any one of embodiments 1) to 11), wherein the $P2Y_{12}$ receptor antagonist is administered and/or is to be administered to a patient by subcutaneous administration and by patient self-administration by use of an auto-injector device.

18) A further embodiment of the invention relates to a $P2Y_{12}$ receptor antagonist (notably Compound 1), or a pharmaceutically acceptable salt thereof, for use according to any one of embodiments 1) to 17), wherein the patient to be treated is a patient with an atherosclerosis disease.

19) A further embodiment of the invention relates to a $P2Y_{12}$ receptor antagonist (notably Compound 1), or a pharmaceutically acceptable salt thereof, for use according to any one of embodiments 1) to 17), wherein the patient to be treated is a patient with a known coronary artery disease who had a prior symptomatic episode of acute coronary syndromes.

20) A further embodiment of the invention relates to a $P2Y_{12}$ receptor antagonist, or a pharmaceutically acceptable salt thereof, for use according to any one of embodiments 1) to 19), wherein the $P2Y_{12}$ receptor antagonist is 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester (Compound 1), or a pharmaceutically acceptable salt thereof.

21) A further embodiment of the invention relates to a $P2Y_{12}$ receptor antagonist, or a pharmaceutically acceptable salt thereof, for use according to any one of embodiments 1) to 19), wherein the $P2Y_{12}$ receptor antagonist is (1S,2S,3R,5S)-3-[7-[(1R,2S)-2-(3,4-difluorophenyl)cyclopropylamino]-5-(propylthio)-3H-[1,2,3]triazolo[4,5-d]pyrimidin-3-yl]-5-(2-hydroxyethoxy)cyclopentane-1,2-diol (Ticagrelor), or a pharmaceutically acceptable salt thereof, or (1 S,2R,3S,4R)-4-[7-[(1R,2S)-2-(3,4-difluorophenyl)cyclopropylamino]-5-(propylthio)-3H-[1,2,3]triazolo[4,5-d]pyrimidin-3-yl]cyclopentane-1,2,3-triol (Ticagrelor-M), or a pharmaceutically acceptable salt thereof. Preferably the $P2Y_{12}$ receptor antagonist is (1 S,2S,3R,5S)-3-[7-[(1R,2S)-2-(3,4-difluorophenyl)cyclopropylamino]-5-(propylthio)-3H-[1,2,3]triazolo[4,5-d]pyrimidin-3-yl]-5-(2-hydroxyethoxy)cyclopentane-1,2-diol (Ticagrelor), or a pharmaceutically acceptable salt thereof.

22) A further embodiment of the invention relates to a $P2Y_{12}$ receptor antagonist (notably Compound 1), or a pharmaceutically acceptable salt thereof, for use according to any one of embodiments 1) to 21), wherein the amount of the $P2Y_{12}$ receptor antagonist (notably Compound 1) that is administered and/or is to be administered is comprised between 1 mg and 75 mg per administration.

Lower limits of the amount of the $P2Y_{12}$ receptor antagonist (notably Compound 1) are 1 mg, 5 mg, 10 mg, and 20 mg. Upper limits are 35 mg, 40 mg, 50 mg, and 75 mg. It is to be understood that each lower limit can be combined with each upper limit. Hence all combinations shall herewith be specifically disclosed. A preferred amount of the $P2Y_{12}$ receptor antagonist (notably Compound 1) is from 10 mg to 40 mg per administration.

In another preferred embodiment, the amount of the $P2Y_{12}$ receptor antagonist (notably Compound 1) is from 5 mg to 20 mg per administration.

23) A further embodiment of the invention relates to a $P2Y_{12}$ receptor antagonist (notably Compound 1), or a pharmaceutically acceptable salt thereof, for use according to any one of embodiments 1) to 22), wherein the $P2Y_{12}$ receptor antagonist (notably Compound 1), optionally together with one or more therapeutically inert excipient(s), is dissolved in a pharmaceutically acceptable liquid to give a solution and wherein the volume of the solution that is administered and/or is to be administered is comprised between 0.1 mL and 3.0 mL per administration.

Lower limits of the volume of the solution are 0.1 mL, 0.2 mL, 0.5 mL, and 0.8 mL. Upper limits are 1.0 mL, 1.4 mL, 2.0 mL, and 3.0 mL. It is to be understood that each lower limit can be combined with each upper limit. Hence all combinations shall herewith be specifically disclosed. A preferred volume of the solution is from 0.5 mL to 1.4 mL.

24) A further embodiment of the invention relates to a $P2Y_{12}$ receptor antagonist (notably Compound 1), or a pharmaceutically acceptable salt thereof, for use according to embodiment 23), wherein the solution is administered and/or is to be administered within an administration time between 1 sec to 90 sec.

Lower limits for the administration time are 1 sec, 3 sec, 5 sec and 8 sec. Upper limits are 15 sec, 30 sec, 60 sec and 90 sec. It is to be understood that each lower limit can be combined with each upper limit. Hence all combinations shall herewith be specifically disclosed. A preferred administration time is from 5 sec to 30 sec.

25) A further embodiment of the invention relates to a $P2Y_{12}$ receptor antagonist (notably Compound 1), or a pharmaceutically acceptable salt thereof, for use according to any one of embodiments 1) to 24), wherein the $P2Y_{12}$ receptor antagonist (notably Compound 1) is administered and/or is to be administered in a bolus injection.

26) A further embodiment of the invention relates to a $P2Y_{12}$ receptor antagonist (notably Compound 1), or a pharmaceutically acceptable salt thereof, for use according to any one of embodiments 1) to 24), wherein the $P2Y_{12}$ receptor antagonist (notably Compound 1) is administered and/or is to be administered in a first subcutaneous injection that is a bolus injection and in at least one further subcutaneous injection.

27) A further embodiment of the invention relates to a $P2Y_{12}$ receptor antagonist (notably Compound 1), or a pharmaceutically acceptable salt thereof, for use according to embodiment 26), wherein the further subcutaneous injection is a continuous injection lasting for up to 5 hours.

It is understood that the continuous injection may last for up to 5 hours, up to 4 hours, up to 3 hours, up to 2 hours, up to 1 hour, up to 30 min or up to 15 min. It is further understood that the continuous injection is administered and/or is to be administered with a lower flow rate than the bolus injection. The flow rate of the continuous injection may be in the range of 0.01% to 10% of the flow rate of the bolus injection. Lower limits of the flow rate of the continuous injection are 0.01%, 0.05%, 0.1% and 0.5% of the flow rate of the bolus injection. Upper limits are 0.5%, 1%, 2%, 5% and 10%. It is to be understood that each lower limit can be combined with each upper limit. Hence all combinations shall herewith be specifically disclosed. The continuous injection may start immediately after the end of the bolus injection or may start with a delay of up to 2 hours, up to 1 hour, up to 30 min or up to 15 min after the end of the bolus injection.

28) A further embodiment of the invention relates to a $P2Y_{12}$ receptor antagonist (notably Compound 1), or a pharmaceutically acceptable salt thereof, for use according to embodiment 26), wherein the further subcutaneous injections are 1 to 10 further bolus injections.

Lower limits of the number of further bolus injections are 1 and 2. Upper limits are 3, 5, 7 and 10. It is to be understood that each lower limit can be combined with each upper limit. Hence all combinations shall herewith be specifically disclosed. The time between any two consecutive bolus injections may be in the range of 5 min to 120 min. Lower limits of the time between any two consecutive bolus injections are 5 min, 10 min, 15 min and 30 min. Upper limits are 30 min, 60 min, 90 min and 120 min. It is to be understood that each lower limit can be combined with each upper limit. Hence all combinations shall herewith be specifically disclosed. The volume that is administered and/or is to be administered in a further bolus injection is in the range of 5% to 100% of the volume of the first bolus injection. Lower limits of the volume of a further bolus injection are 5%, 10%, 20% and 30% of the volume of the first bolus injection. Upper limits are 30%, 50%, 70% and 100%. It is to be understood that each lower limit can be combined with each upper limit. Hence all combinations shall herewith be specifically disclosed.

29) A further embodiment of the invention relates to a $P2Y_{12}$ receptor antagonist (notably Compound 1), or a pharmaceutically acceptable salt thereof, for use according to any one of embodiments 1) to 28), wherein an inhibition of platelet aggregation of at least 75% is reached within 30 min after onset of administration of the $P2Y_{12}$ receptor antagonist in at least 80% of the patients.

30) A further embodiment of the invention relates to a $P2Y_{12}$ receptor antagonist (notably Compound 1), or a pharmaceutically acceptable salt thereof, for use according to embodiment 29), wherein an inhibition of platelet aggregation of at least 80% is reached.

31) A further embodiment of the invention relates to a $P2Y_{12}$ receptor antagonist (notably Compound 1), or a pharmaceutically acceptable salt thereof, for use according to embodiment 29), wherein an inhibition of platelet aggregation of at least 85% is reached.

32) A further embodiment of the invention relates to a $P2Y_{12}$ receptor antagonist (notably Compound 1), or a pharmaceutically acceptable salt thereof, for use according to any one of embodiments 29) to 31), wherein the inhibition of platelet aggregation is reached within 25 min after onset of administration of the $P2Y_{12}$ receptor antagonist in at least 80% of the patients.

33) A further embodiment of the invention relates to a $P2Y_{12}$ receptor antagonist (notably Compound 1), or a pharmaceutically acceptable salt thereof, for use according to any one of embodiments 29) to 31), wherein the inhibition of platelet aggregation is reached within 20 min after onset of administration of the $P2Y_{12}$ receptor antagonist in at least 80% of the patients.

34) A further embodiment of the invention relates to a $P2Y_{12}$ receptor antagonist (notably Compound 1), or a pharmaceutically acceptable salt thereof, for use according to any one of embodiments 29) to 33), wherein the inhibition of platelet aggregation is reached in at least 85% of the patients.

35) A further embodiment of the invention relates to a $P2Y_{12}$ receptor antagonist (notably Compound 1), or a pharmaceutically acceptable salt thereof, for use according to any one of embodiments 29) to 33), wherein the inhibition of platelet aggregation is reached in at least 90% of the patients.

36) A further embodiment of the invention relates to a $P2Y_{12}$ receptor antagonist (notably Compound 1), or a pharmaceutically acceptable salt thereof, for use according to any one of embodiments 1) to 35), wherein an inhibition of platelet aggregation of at least 75% (notably at least 80% and especially at least 85%) is reached in at least 80% of the patients and lasts for at least 3 hours after onset of administration of the $P2Y_{12}$ receptor antagonist.

37) A further embodiment of the invention relates to a $P2Y_{12}$ receptor antagonist (notably Compound 1), or a pharmaceutically acceptable salt thereof, for use according to any one of embodiments 1) to 35), wherein an inhibition of platelet aggregation of at least 75% (notably at least 80% and especially at least 85%) is reached in at least 80% of the patients and lasts for an inhibition time between 3 hours and 12 hours after onset of administration of the $P2Y_{12}$ receptor antagonist.

Lower limits of the inhibition time are 3 hours, and 4 hours. Upper limits are 4 hours, 5 hours, 6 hours, 7 hours, 8 hours, 10 hours and 12 hours. It is to be understood that each lower limit can be combined with each upper limit. Hence all combinations shall herewith be specifically disclosed. A preferred inhibition time is from 4 hours to 8 hours.

38) A further embodiment of the invention relates to a $P2Y_{12}$ receptor antagonist (notably Compound 1), or a pharmaceutically acceptable salt thereof, for use according to any one of embodiments 1) to 37), wherein the $P2Y_{12}$ receptor antagonist is administered to a patient by subcutaneous administration.

39) A further embodiment of the invention relates to a $P2Y_{12}$ receptor antagonist (notably Compound 1), or a pharmaceutically acceptable salt thereof, for use according to any one of embodiments 1) to 37), wherein the $P2Y_{12}$ receptor antagonist is to be administered to a patient by subcutaneous administration.

40) A further embodiment of the invention relates to a pharmaceutical composition comprising, as active principle, a $P2Y_{12}$ receptor antagonist selected from Compound 1, Ticagrelor and Ticagrelor-M (notably Compound 1), or a pharmaceutically acceptable salt thereof, for use according to any one of embodiments 1) to 37), wherein the pharmaceutical composition is administered and/or is to be administered to a patient by subcutaneous administration and wherein the pharmaceutical composition further comprises at least one therapeutically inert excipient.

The production of subcutaneous pharmaceutical compositions of Compound 1 (or Ticagrelor or Ticagrelor-M) can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing Compound 1 (or Ticagrelor or Ticagrelor-M) or a pharmaceutically acceptable salt thereof into a galenical administration form together with suitable, non-toxic, inert, pharmaceutically acceptable solid or liquid carrier materials and, if desired, usual pharmaceutical adjuvants/excipients.

Whenever a $P2Y_{12}$ receptor antagonist (Compound 1 and/or Ticagrelor and/or Ticagrelor-M), or a pharmaceutically acceptable salt thereof, is described to be useful for the prevention or treatment (notably treatment) of a disease, it is understood that the P2Y$_{12}$ receptor antagonist (Compound 1 and/or Ticagrelor and/or Ticagrelor-M), or a pharmaceutically acceptable salt thereof, is also useful for the preparation of a medicament for the prevention or treatment (notably treatment) of said disease. The present invention thus encompasses especially the following additional embodiments:

41) A further embodiment of the invention relates to the use of a P2Y$_{12}$ receptor antagonist selected from Compound 1, Ticagrelor and Ticagrelor-M, or a pharmaceutically acceptable salt thereof, for the preparation of a medicament for use according to any one of embodiments 1) to 39).

42) A further embodiment of the invention relates to the use of Compound 1, or a pharmaceutically acceptable salt thereof, for the preparation of a medicament for use according to any one of embodiments 1) to 20) or 22) to 39).

43) A further embodiment of the invention relates to the use of Compound 1, or a pharmaceutically acceptable salt thereof, for the preparation of a medicament for the treatment of a disease, wherein the disease is selected from acute arterial thromboses and acute venous thromboses, and wherein the medicament is administered and/or is to be administered to a patient by subcutaneous administration.

44) A further embodiment of the invention relates to the use of Compound 1, or a pharmaceutically acceptable salt thereof, for the preparation of a medicament for the treatment of a disease, wherein the disease is selected from acute arterial thromboses, and wherein the medicament is administered and/or is to be administered to a patient by subcutaneous administration.

45) A further embodiment of the invention relates to the use of Compound 1, or a pharmaceutically acceptable salt thereof, for the preparation of a medicament for the treatment of a disease, wherein the disease is selected from acute coronary syndromes, myocardial infarction, peripheral ischaemia, amaurosis, sudden cardiac death, ischaemic stroke and transient ischaemic attack, and wherein the medicament is administered and/or is to be administered to a patient by subcutaneous administration.

46) A further embodiment of the invention relates to the use of Compound 1, or a pharmaceutically acceptable salt thereof, for the preparation of a medicament for the treatment of a disease, wherein the disease is selected from acute coronary syndromes, peripheral ischaemia, amaurosis, ischaemic stroke and transient ischaemic attack, and wherein the medicament is administered and/or is to be administered to a patient by subcutaneous administration.

47) A further embodiment of the invention relates to the use of Compound 1, or a pharmaceutically acceptable salt thereof, for the preparation of a medicament for the treatment of acute coronary syndromes, and wherein the medicament is administered and/or is to be administered to a patient by subcutaneous administration.

48) A further embodiment of the invention relates to the use of Compound 1, or a pharmaceutically acceptable salt thereof, for the preparation of a medicament for the treatment of myocardial infarction, and wherein the medicament is administered and/or is to be administered to a patient by subcutaneous administration.

49) A further embodiment of the invention relates to the use of Compound 1, or a pharmaceutically acceptable salt thereof, for the preparation of a medicament for the treatment of peripheral ischaemia, and wherein the medicament is administered and/or is to be administered to a patient by subcutaneous administration.

50) A further embodiment of the invention relates to the use of Compound 1, or a pharmaceutically acceptable salt thereof, for the preparation of a medicament for the treatment of amaurosis, and wherein the medicament is administered and/or is to be administered to a patient by subcutaneous administration.

51) A further embodiment of the invention relates to the use of Compound 1, or a pharmaceutically acceptable salt thereof, for the preparation of a medicament for the treatment of sudden cardiac death, and wherein the medicament is administered and/or is to be administered to a patient by subcutaneous administration.

52) A further embodiment of the invention relates to the use of Compound 1, or a pharmaceutically acceptable salt thereof, for the preparation of a medicament for the treatment of a disease, wherein the disease is selected from ischaemic stroke and transient ischaemic attack, and wherein the medicament is administered and/or is to be administered to a patient by subcutaneous administration.

53) A further embodiment of the invention relates to the use of Compound 1, or a pharmaceutically acceptable salt thereof, according to any one of embodiments 41) to 52); wherein Compound 1, or the pharmaceutically acceptable salt thereof, is administered to a patient by subcutaneous administration.

54) A further embodiment of the invention relates to the use of Compound 1, or a pharmaceutically acceptable salt thereof, according to any one of embodiments 41) to 52); wherein Compound 1, or the pharmaceutically acceptable salt thereof, is to be administered to a patient by subcutaneous administration.

55) A further embodiment of the invention relates to the use of a P2Y$_{12}$ receptor antagonist selected from Compound 1, Ticagrelor and Ticagrelor-M (preferably Compound 1), or a pharmaceutically acceptable salt thereof, for the preparation of a medicament for use in the emergency treatment of suspected acute coronary syndromes (ACS) by patient self-administration prior to hospitalization; wherein the P2Y$_{12}$ receptor antagonist is administered to a patient by subcutaneous administration.

56) A further embodiment of the invention relates to the use of a P2Y$_{12}$ receptor antagonist selected from Compound 1, Ticagrelor and Ticagrelor-M (preferably Compound 1), or a pharmaceutically acceptable salt thereof, for the preparation of a medicament for use in the emergency treatment of suspected acute coronary syndromes (ACS) by patient self-administration prior to hospitalization; wherein the P2Y$_{12}$ receptor antagonist is to be administered to a patient by subcutaneous administration.

Based on the dependencies of the different embodiments as disclosed hereinabove, especially the following embodiments are thus possible and intended and herewith specifically disclosed in individualized form:

1, 2+1, 3+1, 4+1, 5+1, 6+1, 7+1, 8+1, 9+1, 10+1, 11+1, 11+3+1, 11+5+1, 12+11+1, 12+11+3+1, 12+11+5+1, 13+11+1, 13+11+3+1, 13+11+5+1, 14, 15+1, 15+3+1, 15+5+1, 15+11+1, 15+11+3+1, 15+11+5+1, 15+12+11+1, 15+12+11+3+1, 15+12+11+5+1, 15+14, 16+1, 16+3+1, 16+5+1, 16+11+1, 16+11+3+1, 16+11+5+1, 16+12+11+1, 16+12+11+3+1, 16+12+11+5+1, 16+14, 16+15+1, 16+15+3+1, 16+15+5+1, 16+15+11+1, 16+15+11+3+1, 16+15+11+5+1, 16+15+12+11+1, 16+15+12+11+3+1, 16+15+12+11+5+1, 16+15+14, 17+1, 17+3+1, 17+5+1, 17+11+1, 17+11+3+1, 17+11+5+1, 18+1, 18+3+1, 18+5+1, 18+11+1, 18+11+3+1, 18+11+5+1, 18+12+11+1, 18+12+11+3+1, 18+12+11+5+1, 18+14, 18+15+1, 18+15+3+1, 18+15+5+1, 18+15+11+1, 18+15+11+3+1, 18+15+11+5+1, 18+15+12+11+1,

18+15+12+11+3+1, 18+15+12+11+5+1, 18+15+14, 19+1, 19+3+1, 19+5+1, 19+11+1, 19+11+3+1, 19+11+5+1, 19+12+11+1, 19+12+11+3+1, 19+12+11+5+1, 19+14, 19+15+1, 19+15+3+1, 19+15+5+1, 19+15+11+1, 19+15+11+3+1, 19+15+11+5+1, 19+15+12+11+1, 19+15+12+11+3+1, 19+15+12+11+5+1, 19+15+14, 19+16+1, 19+16+3+1, 19+16+5+1, 19+16+11+1, 19+16+11+3+1, 19+16+11+5+1, 19+16+12+11+1, 19+16+12+11+3+1, 19+16+12+11+5+1, 19+16+14, 19+16+15+1, 19+16+15+3+1, 19+16+15+5+1, 19+16+15+11+1, 19+16+15+11+3+1, 19+16+15+11+5+1, 19+16+15+12+11+1, 19+16+15+12+11+3+1, 19+16+15+12+11+5+1, 19+16+15+14, 20+1, 20+2+1, 20+3+1, 20+4+1, 20+5+1, 20+6+1, 20+7+1, 20+8+1, 20+9+1, 20+10+1, 20+11+1, 20+11+3+1, 20+11+5+1, 20+12+11+1, 20+12+11+3+1, 20+12+11+5+1, 20+13+11+1, 20+13+11+3+1, 20+13+11+5+1, 20+14, 20+15+1, 20+15+3+1, 20+15+5+1, 20+15+11+1, 20+15+11+3+1, 20+15+11+5+1, 20+15+12+11+1, 20+15+12+11+3+1, 20+15+12+11+5+1, 20+15+14, 20+16+1, 20+16+3+1, 20+16+5+1, 20+16+11+1, 20+16+11+3+1, 20+16+11+5+1, 20+16+12+11+1, 20+16+12+11+3+1, 20+16+12+11+5+1, 20+16+14, 20+16+15+1, 20+16+15+3+1, 20+16+15+5+1, 20+16+15+11+1, 20+16+15+11+3+1, 20+16+15+11+5+1, 20+16+15+12+11+1, 20+16+15+12+11+3+1, 20+16+15+12+11+5+1, 20+16+15+14, 20+17+1, 20+17+3+1, 20+17+5+1, 20+17+11+1, 20+17+11+3+1, 20+17+11+5+1, 20+18+1, 20+18+3+1, 20+18+5+1, 20+18+11+1, 20+18+11+3+1, 20+18+11+5+1, 20+18+12+11+1, 20+18+12+11+3+1, 20+18+12+11+5+1, 20+18+14, 20+18+15+1, 20+18+15+3+1, 20+18+15+5+1, 20+18+15+11+1, 20+18+15+11+3+1, 20+18+15+11+5+1, 20+18+15+12+11+1, 20+18+15+12+11+3+1, 20+18+15+12+11+5+1, 20+18+15+14, 20+19+1, 20+19+3+1, 20+19+5+1, 20+19+11+1, 20+19+11+3+1, 20+19+11+5+1, 20+19+12+11+1, 20+19+12+11+3+1, 20+19+12+11+5+1, 20+19+14, 20+19+15+1, 20+19+15+3+1, 20+19+15+5+1, 20+19+15+11+1, 20+19+15+11+3+1, 20+19+15+11+5+1, 20+19+15+12+11+1, 20+19+15+12+11+3+1, 20+19+15+12+11+5+1, 20+19+15+14, 20+19+16+1, 20+19+16+3+1, 20+19+16+5+1, 20+19+16+11+1, 20+19+16+11+3+1, 20+19+16+11+5+1, 20+19+16+12+11+1, 20+19+16+12+11+3+1, 20+19+16+12+11+5+1, 20+19+16+14, 20+19+16+15+1, 20+19+16+15+3+1, 20+19+16+15+5+1, 20+19+16+15+11+1, 20+19+16+15+11+3+1, 20+19+16+15+11+5+1, 20+19+16+15+12+11+1, 20+19+16+15+12+11+3+1, 20+19+16+15+12+11+5+1, 20+19+16+15+14, 21+1, 21+3+1, 21+5+1, 21+11+1, 21+11+3+1, 21+11+5+1, 21+12+11+1, 21+12+11+3+1, 21+12+11+5+1, 22+1, 22+3+1, 22+5+1, 22+11+1, 22+11+3+1, 22+11+5+1, 22+12+11+1, 22+12+11+3+1, 22+12+11+5+1, 22+14, 22+16+1, 22+16+3+1, 22+16+5+1, 22+16+11+1, 22+16+11+3+1, 22+16+11+5+1, 22+16+12+11+1, 22+16+12+11+3+1, 22+16+12+11+5+1, 22+16+14, 22+16+15+1, 22+16+15+3+1, 22+16+15+5+1, 22+16+15+11+1, 22+16+15+11+3+1, 22+16+15+11+5+1, 22+16+15+12+11+1, 22+16+15+12+11+3+1, 22+16+15+12+11+5+1, 22+16+15+14, 22+20+1, 22+20+2+1, 22+20+3+1, 22+20+4+1, 22+20+5+1, 22+20+6+1, 22+20+7+1, 22+20+8+1, 22+20+9+1, 22+20+10+1, 22+20+11+1, 22+20+11+3+1, 22+20+11+5+1, 22+20+12+11+1, 22+20+12+11+3+1, 22+20+12+11+5+1, 22+20+13+11+1, 22+20+13+11+3+1, 22+20+13+11+5+1, 22+20+14, 22+20+15+1, 22+20+15+3+1, 22+20+15+5+1, 22+20+15+11+1, 22+20+15+11+3+1, 22+20+15+11+5+1, 22+20+15+12+11+1, 22+20+15+12+11+3+1, 22+20+15+12+11+5+1, 22+20+15+14, 22+20+16+1, 22+20+16+3+1, 22+20+16+5+1, 22+20+16+11+1, 22+20+16+11+3+1, 22+20+16+11+5+1, 22+20+16+12+11+1, 22+20+16+12+11+3+1, 22+20+16+12+11+5+1, 22+20+16+14, 22+20+16+15+1, 22+20+16+15+3+1, 22+20+16+15+5+1, 22+20+16+15+11+1, 22+20+16+15+11+3+1, 22+20+16+15+11+5+1, 22+20+16+15+12+11+1, 22+20+16+15+12+11+3+1, 22+20+16+15+12+11+5+1, 22+20+16+15+14, 22+20+17+1, 22+20+17+3+1, 22+20+17+5+1, 22+20+17+11+1, 22+20+17+11+3+1, 22+20+17+11+5+1, 22+20+18+1, 22+20+18+3+1, 22+20+18+5+1, 22+20+18+11+1, 22+20+18+11+3+1, 22+20+18+11+5+1, 22+20+18+12+11+1, 22+20+18+12+11+3+1, 22+20+18+12+11+5+1, 22+20+18+14, 22+20+18+15+1, 22+20+18+15+3+1, 22+20+18+15+5+1, 22+20+18+15+11+1, 22+20+18+15+11+3+1, 22+20+18+15+11+5+1, 22+20+18+15+12+11+1, 22+20+18+15+12+11+3+1, 22+20+18+15+12+11+5+1, 22+20+18+15+14, 22+20+19+1, 22+20+19+3+1, 22+20+19+5+1, 22+20+19+11+1, 22+20+19+11+3+1, 22+20+19+11+5+1, 22+20+19+12+11+1, 22+20+19+12+11+3+1, 22+20+19+12+11+5+1, 22+20+19+14, 22+20+19+15+1, 22+20+19+15+3+1, 22+20+19+15+5+1, 22+20+19+15+11+1, 22+20+19+15+11+3+1, 22+20+19+15+11+5+1, 22+20+19+15+12+11+1, 22+20+19+15+12+11+3+1, 22+20+19+15+12+11+5+1, 22+20+19+15+14, 22+20+19+16+1, 22+20+19+16+3+1, 22+20+19+16+5+1, 22+20+19+16+11+1, 22+20+19+16+11+3+1, 22+20+19+16+11+5+1, 22+20+19+16+12+11+1, 22+20+19+16+12+11+3+1, 22+20+19+16+12+11+5+1, 22+20+19+16+14, 22+20+19+16+15+1, 22+20+19+16+15+3+1, 22+20+19+16+15+5+1, 22+20+19+16+15+11+1, 22+20+19+16+15+11+3+1, 22+20+19+16+15+11+5+1, 22+20+19+16+15+12+11+1, 22+20+19+16+15+12+11+3+1, 22+20+19+16+15+12+11+5+1, 22+20+19+16+15+14, 23+1, 23+3+1, 23+5+1, 23+11+1, 23+11+3+1, 23+11+5+1, 23+12+11+1, 23+12+11+3+1, 23+12+11+5+1, 23+14, 23+16+1, 23+16+3+1, 23+16+5+1, 23+16+11+1, 23+16+11+3+1, 23+16+11+5+1, 23+16+12+11+1, 23+16+12+11+3+1, 23+16+12+11+5+1, 23+16+14, 23+16+15+1, 23+16+15+3+1, 23+16+15+5+1, 23+16+15+11+1, 23+16+15+11+3+1, 23+16+15+11+5+1, 23+16+15+12+11+1, 23+16+15+12+11+3+1, 23+16+15+12+11+5+1, 23+16+15+14, 23+20+1, 23+20+2+1, 23+20+3+1, 23+20+4+1, 23+20+5+1, 23+20+6+1, 23+20+7+1, 23+20+8+1, 23+20+9+1, 23+20+10+1, 23+20+11+1, 23+20+11+3+1, 23+20+11+5+1, 23+20+12+11+1, 23+20+12+11+3+1, 23+20+12+11+5+1, 23+20+13+11+1, 23+20+13+11+3+1, 23+20+13+11+5+1, 23+20+14, 23+20+15+1, 23+20+15+3+1, 23+20+15+5+1, 23+20+15+11+1, 23+20+15+11+3+1, 23+20+15+11+5+1, 23+20+15+12+11+1, 23+20+15+12+11+3+1, 23+20+15+12+11+5+1, 23+20+15+14, 23+20+16+1, 23+20+16+3+1, 23+20+16+5+1, 23+20+16+11+1, 23+20+16+11+3+1, 23+20+16+11+5+1, 23+20+16+12+11+1, 23+20+16+12+11+3+1, 23+20+16+12+11+5+1, 23+20+16+14, 23+20+16+15+1, 23+20+16+15+3+1, 23+20+16+15+5+1, 23+20+16+15+11+1, 23+20+16+15+11+3+1, 23+20+16+15+11+5+1, 23+20+16+15+12+11+1, 23+20+16+15+12+11+3+1, 23+20+16+15+12+11+5+1, 23+20+16+15+14, 23+20+17+1, 23+20+17+3+1, 23+20+17+5+1, 23+20+17+11+1, 23+20+17+11+3+1, 23+20+17+11+5+1, 23+20+18+1, 23+20+18+3+1, 23+20+18+5+1, 23+20+18+11+1, 23+20+18+11+3+1, 23+20+18+11+5+1, 23+20+18+12+11+1, 23+20+18+12+11+3+1, 23+20+18+12+11+5+1, 23+20+18+14, 23+20+18+15+1, 23+20+18+15+3+1, 23+20+18+15+5+1, 23+20+18+15+11+1, 23+20+18+15+11+3+1, 23+20+18+15+11+5+1, 23+20+18+15+12+11+1, 23+20+18+15+12+11+3+1, 23+20+18+15+12+11+5+1, 23+20+18+15+14, 23+20+19+1, 23+20+19+3+1, 23+20+19+5+1, 23+20+19+11+1, 23+20+19+11+3+1, 23+20+19+11+5+1, 23+20+19+12+11+1, 23+20+19+12+11+3+1, 23+20+19+12+11+5+1, 23+20+19+14, 23+20+19+15+1, 23+20+19+15+3+1, 23+20+19+15+5+1, 23+20+19+15+11+1, 23+20+19+15+11+3+1, 23+20+19+15+11+5+1,

23+20+19+15+12+11+1, 23+20+19+15+12+11+3+1, 23+20+19+15+12+11+5+1, 23+20+19+15+14, 23+20+19+16+1, 23+20+19+16+3+1, 23+20+19+16+5+1, 23+20+19+16+11+1, 23+20+19+16+11+3+1, 23+20+19+16+11+5+1, 23+20+19+16+12+11+1, 23+20+19+16+12+11+3+1, 23+20+19+16+12+11+5+1, 23+20+19+16+14, 23+20+19+16+15+1, 23+20+19+16+15+3+1, 23+20+19+16+15+5+1, 23+20+19+16+15+11+1, 23+20+19+16+15+11+3+1, 23+20+19+16+15+11+5+1, 23+20+19+16+15+12+11+1, 23+20+19+16+15+12+11+3+1, 23+20+19+16+15+12+11+5+1, 23+20+19+16+15+14, 24+1, 24+3+1, 24+5+1, 24+11+1, 24+11+3+1, 24+11+5+1, 24+12+11+1, 24+12+11+3+1, 24+12+11+5+1, 24+14, 24+16+1, 24+16+3+1, 24+16+5+1, 24+16+11+1, 24+16+11+3+1, 24+16+11+5+1, 24+16+12+11+1, 24+16+12+11+3+1, 24+16+12+11+5+1, 24+16+14, 24+16+15+1, 24+16+15+3+1, 24+16+15+5+1, 24+16+15+11+1, 24+16+15+11+3+1, 24+16+15+11+5+1, 24+16+15+12+11+1, 24+16+15+12+11+3+1, 24+16+15+12+11+5+1, 24+16+15+14, 24+20+1, 24+20+2+1, 24+20+3+1, 24+20+4+1, 24+20+5+1, 24+20+6+1, 24+20+7+1, 24+20+8+1, 24+20+9+1, 24+20+10+1, 24+20+11+1, 24+20+11+3+1, 24+20+11+5+1, 24+20+12+11+1, 24+20+12+11+3+1, 24+20+12+11+5+1, 24+20+13+11+1, 24+20+13+11+3+1, 24+20+13+11+5+1, 24+20+14, 24+20+15+1, 24+20+15+3+1, 24+20+15+5+1, 24+20+15+11+1, 24+20+15+11+3+1, 24+20+15+11+5+1, 24+20+15+12+11+1, 24+20+15+12+11+3+1, 24+20+15+12+11+5+1, 24+20+15+14, 24+20+16+1, 24+20+16+3+1, 24+20+16+5+1, 24+20+16+11+1, 24+20+16+11+3+1, 24+20+16+11+5+1, 24+20+16+12+11+1, 24+20+16+12+11+3+1, 24+20+16+12+11+5+1, 24+20+16+14, 24+20+16+15+1, 24+20+16+15+3+1, 24+20+16+15+5+1, 24+20+16+15+5+1, 24+20+16±15+11±3+1, 24+20+16+15+11+5+1, 24+20+16+15+12+11+1, 24+20+16+15+12+11+3+1, 24+20+16+15+12+11+5+1, 24+20+16+15+14, 24+20+17+1, 24+20+17+3+1, 24+20+17+5+1, 24+20+17+11+1, 24+20+17+11+3+1, 24+20+17+11+5+1, 24+20+18+1, 24+20+18+3+1, 24+20+18+5+1, 24+20+18+11+1, 24+20+18+11+3+1, 24+20+18+11+5+1, 24+20+18+12+11+1, 24+20+18+12+11+3+1, 24+20+18+12+11+5+1, 24+20+18+14, 24+20+18+15+1, 24+20+18+15+3+1, 24+20+18+15+5+1, 24+20+18+15+11+1, 24+20+18+15+11+3+1, 24+20+18+15+11+5+1, 24+20+18+15+12+11+1, 24+20+18+15+12+11+3+1, 24+20+18+15+12+11+5+1, 24+20+18+15+14, 24+20+19+1, 24+20+19+3+1, 24+20+19+5+1, 24+20+19+11+1, 24+20+19+11+3+1, 24+20+19+11+5+1, 24+20+19+12+11+1, 24+20+19+12+11+3+1, 24+20+19+12+11+5+1, 24+20+19+14, 24+20+19+15+1, 24+20+19+15+3+1, 24+20+19+15+5+1, 24+20+19+15+11+1, 24+20+19+15+11+3+1, 24+20+19+15+11+5+1, 24+20+19+15+12+11+1, 24+20+19+15+12+11+3+1, 24+20+19+15+12+11+5+1, 24+20+19+15+14, 24+20+19+16+1, 24+20+19+16+3+1, 24+20+19+16+5+1, 24+20+19+16+11+1, 24+20+19+16+11+3+1, 24+20+19+16+11+5+1, 24+20+19+16+12+11+1, 24+20+19+16+12+11+3+1, 24+20+19+16+12+11+5+1, 24+20+19+16+14, 24+20+19+16+15+1, 24+20+19+16+15+3+1, 24+20+19+16+15+5+1, 24+20+19+16+15+11+1, 24+20+19+16+15+11+3+1, 24+20+19+16+15+11+5+1, 24+20+19+16+15+12+11+1, 24+20+19+16+15+12+11+3+1, 24+20+19+16+15+12+11+5+1, 24+20+19+16+15+14, 24+22+1, 24+22+3+1, 24+22+5+1, 24+22+11+1, 24+22+11+3+1, 24+22+11+5+1, 24+22+12+11+1, 24+22+12+11+3+1, 24+22+12+11+5+1, 24+22+14, 24+22+16+1, 24+22+16+3+1, 24+22+16+5+1, 24+22+16+11+1, 24+22+16+11+3+1, 24+22+16+11+5+1, 24+22+16+12+11+1, 24+22+16+12+11+3+1, 24+22+16+12+11+5+1, 24+22+16+14, 24+22+16+15+1, 24+22+16+15+3+1, 24+22+16+15+5+1, 24+22+16+15+11+1, 24+22+16+15+11+3+1, 24+22+16+15+11+5+1, 24+22+16+15+12+11+1, 24+22+16+15+12+11+3+1, 24+22+16+15+12+11+5+1, 24+22+16+15+14, 24+22+20+1, 24+22+20+2+1, 24+22+20+3+1, 24+22+20+4+1, 24+22+20+5+1, 24+22+20+6+1, 24+22+20+7+1, 24+22+20+8+1, 24+22+20+9+1, 24+22+20+10+1, 24+22+20+11+1, 24+22+20+11+3+1, 24+22+20+11+5+1, 24+22+20+12+11+1, 24+22+20+12+11+3+1, 24+22+20+12+11+5+1, 24+22+20+13+11+1, 24+22+20+13+11+3+1, 24+22+20+13+11+5+1, 24+22+20+14, 24+22+20+15+1, 24+22+20+15+3+1, 24+22+20+15+5+1, 24+22+20+15+11+1, 24+22+20+15+11+3+1, 24+22+20+15+11+5+1, 24+22+20+15+12+11+1, 24+22+20+15+12+11+3+1, 24+22+20+15+12+11+5+1, 24+22+20+15+14, 24+22+20+16+1, 24+22+20+16+3+1, 24+22+20+16+5+1, 24+22+20+16+11+1, 24+22+20+16+11+3+1, 24+22+20+16+11+5+1, 24+22+20+16+12+11+1, 24+22+20+16+12+11+3+1, 24+22+20+16+12+11+5+1, 24+22+20+16+14, 24+22+20+16+15+1, 24+22+20+16+15+3+1, 24+22+20+16+15+5+1, 24+22+20+16+15+11+1, 24+22+20+16+15+11+3+1, 24+22+20+16+15+11+5+1, 24+22+20+16+15+12+11+1, 24+22+20+16+15+12+11+3+1, 24+22+20+16+15+12+11+5+1, 24+22+20+16+15+14, 24+22+20+17+1, 24+22+20+17+3+1, 24+22+20+17+5+1, 24+22+20+17+11+1, 24+22+20+17+11+3+1, 24+22+20+17+11+5+1, 24+22+20+18+1, 24+22+20+18+3+1, 24+22+20+18+5+1, 24+22+20+18+11+1, 24+22+20+18+11+3+1, 24+22+20+18+11+5+1, 24+22+20+18+12+11+1, 24+22+20+18+12+11+3+1, 24+22+20+18+12+11+5+1, 24+22+20+18+14, 24+22+20+18+15+1, 24+22+20+18+15+3+1, 24+22+20+18+15+5+1, 24+22+20+18+15+11+1, 24+22+20+18+15+11+3+1, 24+22+20+18+15+11+5+1, 24+22+20+18+15+12+11+1, 24+22+20+18+15+12+11+3+1, 24+22+20+18+15+12+11+5+1, 24+22+20+18+15+14, 24+22+20+19+1, 24+22+20+19+3+1, 24+22+20+19+5+1, 24+22+20+19+11+1, 24+22+20+19+11+3+1, 24+22+20+19+11+5+1, 24+22+20+19+12+11+1, 24+22+20+19+12+11+3+1, 24+22+20+19+12+11+5+1, 24+22+20+19+14, 24+22+20+19+15+1, 24+22+20+19+15+3+1, 24+22+20+19+15+5+1, 24+22+20+19+15+11+1, 24+22+20+19+15+11+3+1, 24+22+20+19+15+11+5+1, 24+22+20+19+15+12+11+1, 24+22+20+19+15+12+11+3+1, 24+22+20+19+15+12+11+5+1, 24+22+20+19+15+14, 24+22+20+19+16+1, 24+22+20+19+16+3+1, 24+22+20+19+16+5+1, 24+22+20+19+16+11+1, 24+22+20+19+16+11+3+1, 24+22+20+19+16+11+5+1, 24+22+20+19+16+12+11+1, 24+22+20+19+16+12+11+3+1, 24+22+20+19+16+12+11+5+1, 24+22+20+19+16+14, 24+22+20+19+16+15+1, 24+22+20+19+16+15+3+1, 24+22+20+19+16+15+5+1, 24+22+20+19+16+15+11+1, 24+22+20+19+16+15+11+3+1, 24+22+20+19+16+15+11+5+1, 24+22+20+19+16+15+12+11+1, 24+22+20+19+16+15+12+11+3+1, 24+22+20+19+16+15+12+11+5+1, 24+22+20+19+16+15+14, 25+1, 25+3+1, 25+5+1, 25+11+1, 25+11+3+1, 25+11+5+1, 25+12+11+1, 25+12+11+3+1, 25+12+11+5+1, 25+14, 25+16+1, 25+16+3+1, 25+16+5+1, 25+16+11+1, 25+16+11+3+1, 25+16+11+5+1, 25+16+12+11+1, 25+16+12+11+3+1, 25+16+12+11+5+1, 25+16+14, 25+16+15+1, 25+16+15+3+1, 25+16+15+5+1, 25+16+15+11+1, 25+16+15+11+3+1, 25+16+15+11+5+1, 25+16+15+12+11+1, 25+16+15+12+11+3+1, 25+16+15+12+11+5+1, 25+16+15+14, 25+20+1, 25+20+2+1, 25+20+3+1, 25+20+4+1, 25+20+5+1, 25+20+6+1, 25+20+7+1, 25+20+8+1, 25+20+9+1, 25+20+10+1, 25+20+11+1, 25+20+11+3+1, 25+20+11+5+1, 25+20+12+11+1, 25+20+12+11+3+1, 25+20+12+11+5+1, 25+20+13+11+1, 25+20+13+11+3+1, 25+20+13+11+5+1, 25+20+14, 25+20+15+1, 25+20+15+3+1, 25+20+15+5+1, 25+20+15+11+1, 25+20+15+11+3+1, 25+20+15+11+5+1, 25+20+15+12+11+1,

25+20+15+12+11+3+1, 25+20+15+12+11+5+1, 25+20+15+14, 25+20+16+1, 25+20+16+3+1, 25+20+16+5+1, 25+20+16+11+1, 25+20+16+11+3+1, 25+20+16+11+5+1, 25+20+16+12+11+1, 25+20+16+12+11+3+1, 25+20+16+12+11+5+1, 25+20+16+14, 25+20+16+15+1, 25+20+16+15+3+1, 25+20+16+15+5+1, 25+20+16+15+11+1, 25+20+16+15+11+3+1, 25+20+16+15+11+5+1, 25+20+16+15+12+11+1, 25+20+16+15+12+11+3+1, 25+20+16+15+12+11+5+1, 25+20+16+15+14, 25+20+17+1, 25+20+17+3+1, 25+20+17+5+1, 25+20+17+11+1, 25+20+17+11+3+1, 25+20+17+11+5+1, 25+20+18+1, 25+20+18+3+1, 25+20+18+5+1, 25+20+18+11+1, 25+20+18+11+3+1, 25+20+18+11+5+1, 25+20+18+12+11+1, 25+20+18+12+11+3+1, 25+20+18+12+11+5+1, 25+20+18+14, 25+20+18+15+1, 25+20+18+15+3+1, 25+20+18+15+5+1, 25+20+18+15+11+1, 25+20+18+15+11+3+1, 25+20+18+15+11+5+1, 25+20+18+15+12+11+1, 25+20+18+15+12+11+3+1, 25+20+18+15+12+11+5+1, 25+20+18+15+14, 25+20+19+1, 25+20+19+3+1, 25+20+19+5+1, 25+20+19+11+1, 25+20+19+11+3+1, 25+20+19+11+5+1, 25+20+19+12+11+1, 25+20+19+12+11+3+1, 25+20+19+12+11+5+1, 25+20+19+14, 25+20+19+15+1, 25+20+19+15+3+1, 25+20+19+15+5+1, 25+20+19+15+11+1, 25+20+19+15+11+3+1, 25+20+19+15+11+5+1, 25+20+19+15+12+11+1, 25+20+19+15+12+11+3+1, 25+20+19+15+12+11+5+1, 25+20+19+15+14, 25+20+19+16+1, 25+20+19+16+3+1, 25+20+19+16+5+1, 25+20+19+16+11+1, 25+20+19+16+11+3+1, 25+20+19+16+11+5+1, 25+20+19+16+12+11+1, 25+20+19+16+12+11+3+1, 25+20+19+16+12+11+5+1, 25+20+19+16+14, 25+20+19+16+15+1, 25+20+19+16+15+3+1, 25+20+19+16+15+5+1, 25+20+19+16+15+11+1, 25+20+19+16+15+11+3+1, 25+20+19+16+15+11+5+1, 25+20+19+16+15+12+11+1, 25+20+19+16+15+12+11+3+1, 25+20+19+16+15+12+11+5+1, 25+20+19+16+15+14, 25+22+1, 25+22+3+1, 25+22+5+1, 25+22+11+1, 25+22+11+3+1, 25+22+11+5+1, 25+22+12+11+1, 25+22+12+11+3+1, 25+22+12+11+5+1, 25+22+14, 25+22+16+1, 25+22+16+3+1, 25+22+16+5+1, 25+22+16+11+1, 25+22+16+11+3+1, 25+22+16+11+5+1, 25+22+16+12+11+1, 25+22+16+12+11+3+1, 25+22+16+12+11+5+1, 25+22+16+14, 25+22+16+15+1, 25+22+16+15+3+1, 25+22+16+15+5+1, 25+22+16+15+11+1, 25+22+16+15+11+3+1, 25+22+16+15+11+5+1, 25+22+16+15+12+11+1, 25+22+16+15+12+11+3+1, 25+22+16+15+12+11+5+1, 25+22+16+15+14, 25+22+20+1, 25+22+20+2+1, 25+22+20+3+1, 25+22+20+4+1, 25+22+20+5+1, 25+22+20+6+1, 25+22+20+7+1, 25+22+20+8+1, 25+22+20+9+1, 25+22+20+10+1, 25+22+20+11+1, 25+22+20+11+3+1, 25+22+20+11+5+1, 25+22+20+12+11+1, 25+22+20+12+11+3+1, 25+22+20+12+11+5+1, 25+22+20+13+11+1, 25+22+20+13+11+3+1, 25+22+20+13+11+5+1, 25+22+20+14, 25+22+20+15+1, 25+22+20+15+3+1, 25+22+20+15+5+1, 25+22+20+15+11+1, 25+22+20+15+11+3+1, 25+22+20+15+11+5+1, 25+22+20+15+12+11+1, 25+22+20+15+12+11+3+1, 25+22+20+15+12+11+5+1, 25+22+20+15+14, 25+22+20+16+1, 25+22+20+16+3+1, 25+22+20+16+5+1, 25+22+20+16+11+1, 25+22+20+16+11+3+1, 25+22+20+16+11+5+1, 25+22+20+16+12+11+1, 25+22+20+16+12+11+3+1, 25+22+20+16+12+11+5+1, 25+22+20+16+14, 25+22+20+16+15+1, 25+22+20+16+15+3+1, 25+22+20+16+15+5+1, 25+22+20+16+15+11+1, 25+22+20+16+15+11+3+1, 25+22+20+16+15+11+5+1, 25+22+20+16+15+12+11+1, 25+22+20+16+15+12+11+3+1, 25+22+20+16+15+12+11+5+1, 25+22+20+16+15+14, 25+22+20+17+1, 25+22+20+17+3+1, 25+22+20+17+5+1, 25+22+20+17+11+1, 25+22+20+17+11+3+1, 25+22+20+17+11+5+1, 25+22+20+18+1, 25+22+20+18+3+1, 25+22+20+18+5+1, 25+22+20+18+11+1, 25+22+20+18+11+3+1, 25+22+20+18+11+5+1, 25+22+20+18+12+11+1, 25+22+20+18+12+11+3+1, 25+22+20+18+12+11+5+1, 25+22+20+18+14, 25+22+20+18+15+1, 25+22+20+18+15+3+1, 25+22+20+18+15+5+1, 25+22+20+18+15+11+1, 25+22+20+18+15+11+3+1, 25+22+20+18+15+11+5+1, 25+22+20+18+15+12+11+1, 25+22+20+18+15+12+11+3+1, 25+22+20+18+15+12+11+5+1, 25+22+20+18+15+14, 25+22+20+19+1, 25+22+20+19+3+1, 25+22+20+19+5+1, 25+22+20+19+11+1, 25+22+20+19+11+3+1, 25+22+20+19+11+5+1, 25+22+20+19+12+11+1, 25+22+20+19+12+11+3+1, 25+22+20+19+12+11+5+1, 25+22+20+19+14, 25+22+20+19+15+1, 25+22+20+19+15+3+1, 25+22+20+19+15+5+1, 25+22+20+19+15+11+1, 25+22+20+19+15+11+3+1, 25+22+20+19+15+11+5+1, 25+22+20+19+15+12+11+1, 25+22+20+19+15+12+11+3+1, 25+22+20+19+15+12+11+5+1, 25+22+20+19+15+14, 25+22+20+19+16+1, 25+22+20+19+16+3+1, 25+22+20+19+16+5+1, 25+22+20+19+16+11+1, 25+22+20+19+16+11+3+1, 25+22+20+19+16+11+5+1, 25+22+20+19+16+12+11+1, 25+22+20+19+16+12+11+3+1, 25+22+20+19+16+12+11+5+1, 25+22+20+19+16+14, 25+22+20+19+16+15+1, 25+22+20+19+16+15+3+1, 25+22+20+19+16+15+5+1, 25+22+20+19+16+15+11+1, 25+22+20+19+16+15+11+3+1, 25+22+20+19+16+15+11+5+1, 25+22+20+19+16+15+12+11+1, 25+22+20+19+16+15+12+11+3+1, 25+22+20+19+16+15+12+11+5+1, 25+22+20+19+16+15+14, 26+1, 26+3+1, 26+5+1, 26+11+1, 26+11+3+1, 26+11+5+1, 26+12+11+1, 26+12+11+3+1, 26+12+11+5+1, 26+14, 26+16+1, 26+16+3+1, 26+16+5+1, 26+16+11+1, 26+16+11+3+1, 26+16+11+5+1, 26+16+12+11+1, 26+16+12+11+3+1, 26+16+12+11+5+1, 26+16+14, 26+16+15+1, 26+16+15+3+1, 26+16+15+5+1, 26+16+15+11+1, 26+16+15+11+3+1, 26+16+15+11+5+1, 26+16+15+12+11+1, 26+16+15+12+11+3+1, 26+16+15+12+11+5+1, 26+16+15+14, 26+20+1, 26+20+2+1, 26+20+3+1, 26+20+4+1, 26+20+5+1, 26+20+6+1, 26+20+7+1, 26+20+8+1, 26+20+9+1, 26+20+10+1, 26+20+11+1, 26+20+11+3+1, 26+20+11+5+1, 26+20+12+11+1, 26+20+12+11+3+1, 26+20+12+11+5+1, 26+20+13+11+1, 26+20+13+11+3+1, 26+20+13+11+5+1, 26+20+14, 26+20+15+1, 26+20+15+3+1, 26+20+15+5+1, 26+20+15+11+1, 26+20+15+11+3+1, 26+20+15+11+5+1, 26+20+15+12+11+1, 26+20+15+12+11+3+1, 26+20+15+12+11+5+1, 26+20+15+14, 26+20+16+1, 26+20+16+3+1, 26+20+16+5+1, 26+20+16+11+1, 26+20+16+11+3+1, 26+20+16+11+5+1, 26+20+16+12+11+1, 26+20+16+12+11+3+1, 26+20+16+12+11+5+1, 26+20+16+14, 26+20+16+15+1, 26+20+16+15+3+1, 26+20+16+15+5+1, 26+20+16+15+11+1, 26+20+16+15+11+3+1, 26+20+16+15+11+5+1, 26+20+16+15+12+11+1, 26+20+16+15+12+11+3+1, 26+20+16+15+12+11+5+1, 26+20+16+15+14, 26+20+17+1, 26+20+17+3+1, 26+20+17+5+1, 26+20+17+11+1, 26+20+17+11+3+1, 26+20+17+11+5+1, 26+20+18+1, 26+20+18+3+1, 26+20+18+5+1, 26+20+18+11+1, 26+20+18+11+3+1, 26+20+18+11+5+1, 26+20+18+12+11+1, 26+20+18+12+11+3+1, 26+20+18+12+11+5+1, 26+20+18+14, 26+20+18+15+1, 26+20+18+15+3+1, 26+20+18+15+5+1, 26+20+18+15+11+1, 26+20+18+15+11+3+1, 26+20+18+15+11+5+1, 26+20+18+15+12+11+1, 26+20+18+15+12+11+3+1, 26+20+18+15+12+11+5+1, 26+20+18+15+14, 26+20+19+1, 26+20+19+3+1, 26+20+19+5+1, 26+20+19+11+1, 26+20+19+11+3+1, 26+20+19+11+5+1, 26+20+19+12+11+1, 26+20+19+12+11+3+1, 26+20+19+12+11+5+1, 26+20+19+14, 26+20+19+15+1, 26+20+19+15+3+1, 26+20+19+15+5+1, 26+20+19+15+11+1, 26+20+19+15+11+3+1, 26+20+19+15+11+5+1, 26+20+19+15+12+11+1, 26+20+19+15+12+11+3+1, 26+20+19+15+12+11+5+1, 26+20+19+15+14, 26+20+19+16+1, 26+20+19+16+3+1,

26+20+19+16+5+1, 26+20+19+16+11+1, 26+20+19+16+11+3+1, 26+20+19+16+11+5+1, 26+20+19+16+12+11+1, 26+20+19+16+12+11+3+1, 26+20+19+16+12+11+5+1, 26+20+19+16+14, 26+20+19+16+15+1, 26+20+19+16+15+3+1, 26+20+19+16+15+5+1, 26+20+19+16+15+11+1, 26+20+19+16+15+11+3+1, 26+20+19+16+15+11+5+1, 26+20+19+16+15+12+11+1, 26+20+19+16+15+12+11+3+1, 26+20+19+16+15+12+11+5+1, 26+20+19+16+15+14, 26+22+1, 26+22+3+1, 26+22+5+1, 26+22+11+1, 26+22+11+3+1, 26+22+11+5+1, 26+22+12+11+1, 26+22+12+11+3+1, 26+22+12+11+5+1, 26+22+14, 26+22+16+1, 26+22+16+3+1, 26+22+16+5+1, 26+22+16+11+1, 26+22+16+11+3+1, 26+22+16+11+5+1, 26+22+16+12+11+1, 26+22+16+12+11+3+1, 26+22+16+12+11+5+1, 26+22+16+14, 26+22+16+15+1, 26+22+16+15+3+1, 26+22+16+15+5+1, 26+22+16+15+11+1, 26+22+16+15+11+3+1, 26+22+16+15+11+5+1, 26+22+16+15+12+11+1, 26+22+16+15+12+11+3+1, 26+22+16+15+12+11+5+1, 26+22+16+15+14, 26+22+20+1, 26+22+20+2+1, 26+22+20+3+1, 26+22+20+4+1, 26+22+20+5+1, 26+22+20+6+1, 26+22+20+7+1, 26+22+20+8+1, 26+22+20+9+1, 26+22+20+10+1, 26+22+20+11+1, 26+22+20+11+3+1, 26+22+20+11+5+1, 26+22+20+12+11+1, 26+22+20+12+11+3+1, 26+22+20+12+11+5+1, 26+22+20+13+11+1, 26+22+20+13+11+3+1, 26+22+20+13+11+5+1, 26+22+20+14, 26+22+20+15+1, 26+22+20+15+3+1, 26+22+20+15+5+1, 26+22+20+15+11+1, 26+22+20+15+11+3+1, 26+22+20+15+11+5+1, 26+22+20+15+12+11+1, 26+22+20+15+12+11+3+1, 26+22+20+15+12+11+5+1, 26+22+20+15+14, 26+22+20+16+1, 26+22+20+16+3+1, 26+22+20+16+5+1, 26+22+20+16+11+1, 26+22+20+16+11+3+1, 26+22+20+16+11+5+1, 26+22+20+16+12+11+1, 26+22+20+16+12+11+3+1, 26+22+20+16+12+11+5+1, 26+22+20+16+14, 26+22+20+16+15+1, 26+22+20+16+15+3+1, 26+22+20+16+15+5+1, 26+22+20+16+15+11+1, 26+22+20+16+15+11+3+1, 26+22+20+16+15+11+5+1, 26+22+20+16+15+12+11+1, 26+22+20+16+15+12+11+3+1, 26+22+20+16+15+12+11+5+1, 26+22+20+16+15+14, 26+22+20+17+1, 26+22+20+17+3+1, 26+22+20+17+5+1, 26+22+20+17+11+1, 26+22+20+17+11+3+1, 26+22+20+17+11+5+1, 26+22+20+18+1, 26+22+20+18+3+1, 26+22+20+18+5+1, 26+22+20+18+11+1, 26+22+20+18+11+3+1, 26+22+20+18+11+5+1, 26+22+20+18+12+11+1, 26+22+20+18+12+11+3+1, 26+22+20+18+12+11+5+1, 26+22+20+18+14, 26+22+20+18+15+1, 26+22+20+18+15+3+1, 26+22+20+18+15+5+1, 26+22+20+18+15+11+1, 26+22+20+18+15+11+3+1, 26+22+20+18+15+11+5+1, 26+22+20+18+15+12+11+1, 26+22+20+18+15+12+11+3+1, 26+22+20+18+15+12+11+5+1, 26+22+20+18+15+14, 26+22+20+19+1, 26+22+20+19+3+1, 26+22+20+19+5+1, 26+22+20+19+11+1, 26+22+20+19+11+3+1, 26+22+20+19+11+5+1, 26+22+20+19+12+11+1, 26+22+20+19+12+11+3+1, 26+22+20+19+12+11+5+1, 26+22+20+19+14, 26+22+20+19+15+1, 26+22+20+19+15+3+1, 26+22+20+19+15+5+1, 26+22+20+19+15+11+1, 26+22+20+19+15+11+3+1, 26+22+20+19+15+11+5+1, 26+22+20+19+15+12+11+1, 26+22+20+19+15+12+11+3+1, 26+22+20+19+15+12+11+5+1, 26+22+20+19+15+14, 26+22+20+19+16+1, 26+22+20+19+16+3+1, 26+22+20+19+16+5+1, 26+22+20+19+16+11+1, 26+22+20+19+16+11+3+1, 26+22+20+19+16+11+5+1, 26+22+20+19+16+12+11+1, 26+22+20+19+16+12+11+3+1, 26+22+20+19+16+12+11+5+1, 26+22+20+19+16+14, 26+22+20+19+16+15+1, 26+22+20+19+16+15+3+1, 26+22+20+19+16+15+5+1, 26+22+20+19+16+15+11+1, 26+22+20+19+16+15+11+3+1, 26+22+20+19+16+15+11+5+1, 26+22+20+19+16+15+12+11+1, 26+22+20+19+16+15+12+11+3+1, 26+22+20+19+16+15+12+11+5+1, 26+22+20+19+16+15+14, 27+26+1, 27+26+3+1, 27+26+5+1, 27+26+11+1, 27+26+11+3+1, 27+26+11+5+1, 27+26+12+11+1, 27+26+12+11+3+1, 27+26+12+11+5+1, 27+26+1, 27+26+11+5+1, 27+2614, 27+26+16+1, 27+26+16+3+1, 27+26+16+5+1, 27+26+16+11+1, 27+26+16+11+3+1, 2726+16±11±5±1, 27+26±16±12+11±1, 27+26+16+12+11+3+1, 27+26+16+12+11+5+1, 27+26+16+14, 27+26+16+15+1, 27+26+16+15+3+1, 27+26+16+15+5+1, 27+26+16+15+11+1, 27+26+16+15+11+3+1, 27+26+16+15+11+5+1, 27+26+16+15+12+11+1, 27+26+16+15+12+11+3+1, 27+26+16+15+12+11+5+1, 27+26+16+15+14, 27+26+20+1, 27+26+20+2+1, 27+26+20+3+1, 27+26+20+4+1, 27+26+20+5+1, 27+26+20+6+1, 27+26+20+7+1, 27+26+20+8+1, 27+26+20+9+1, 27+26+20+10+1, 27+26+20+11+1, 27+26+20+11+3+1, 27+26+20+11+5+1, 27+26+20+12+11+1, 27+26+20+12+11+3+1, 27+26+20+12+11+5+1, 27+26+20+13+11+1, 27+26+20+13+11+3+1, 27+26+20+13+11+5+1, 27+26+20+14, 27+26+20+15+1, 27+26+20+15+3+1, 27+26+20+15+5+1, 27+26+20+15+11+1, 27+26+20+15+11+3+1, 27+26+20+15+11+5+1, 27+26+20+15+12+11+1, 27+26+20+15+12+11+3+1, 27+26+20+15+12+11+5+1, 27+26+20+15+14, 27+26+20+16+1, 27+26+20+16+3+1, 27+26+20+16+5+1, 27+26+20+16+11+1, 27+26+20+16+11+3+1, 27+26+20+16+11+5+1, 27+26+20+16+12+11+1, 27+26+20+16+12+11+3+1, 27+26+20+16+12+11+5+1, 27+26+20+16+14, 27+26+20+16+15+1, 27+26+20+16+15+3+1, 27+26+20+16+15+5+1, 27+26+20+16+15+11+1, 27+26+20+16+15+11+3+1, 27+26+20+16+15+11+5+1, 27+26+20+16+15+12+11+1, 27+26+20+16+15+12+11+3+1, 27+26+20+16+15+12+11+5+1, 27+26+20+16+15+14, 27+26+20+17+1, 27+26+20+17+3+1, 27+26+20+17+5+1, 27+26+20+17+11+1, 27+26+20+17+11+3+1, 27+26+20+17+11+5+1, 27+26+20+18+1, 27+26+20+18+3+1, 27+26+20+18+5+1, 27+26+20+18+11+1, 27+26+20+18++11+1, 27+26+20+18+11+3+1, 27+26+20+18+11+5+1, 27+26+20+18+12+11+1, 27+26+20+18+12+11+3+1, 27+26+20+18+12+11+5+1, 27+26+20+18+14, 27+26+20+18+15+1, 27+26+20+18+15+3+1, 27+26+20+18+15+5+1, 27+26+20+18+15+11+1, 27+26+20+18+15+11+3+1, 27+26+20+18+15+11+5+1, 27+26+20+18+15+12+11+1, 27+26+20+18+15+12+11+3+127+26+20+18+15+12+11+5+1, 27+26+20+18+15+14, 27+26+20+18+15+12+11+5+1, 27+26+20+18+15+14, 27+26+20+19+1, 27+26+20+19+3+1, 27+26+20+19+5+1, 27+26+20+19+11+1, 27+26+20+19+11+3+1, 27+26+20+19+11+5+1, 27+26+20+19+12+11+1, 27+26+20+19+12+11+3+1, 27+26+20+19+12+11+5+1, 27+26+20+19+14, 27+26+20+19+15+1, 27+26+20+19+15+3+1, 27+26+20+19+15+5+1, 27+26+20+19+15+11+1, 27+26+20+19+15+11+3+1, 27+26+20+19+15+11+5+1, 27+26+20+19+15+12+11+1, 27+26+20+19+15+12+11+3+1, 2726+20+19+15+12+11+5+1, 27+26+20+19+15+14, 27+26+20+19+16+1, 27+26+20+19+16+3+1, 27+26+20+19+16+5+1, 27+26+20+19+16+11+1, 27+26+20+19+16+11+3+1, 27+26+20+19+16+11+5+1, 27+26+20+19+16+12+11+1, 27+26+20+19+16+12+11+3+1, 27+26+20+19+16+12+11+5+1, 27+26+20+19+16+14, 27+26+20+19+16+15+1, 27+26+20+19+16+15+3+1, 27+26+20+19+16+15+5+1, 27+26+20+19+16+15+11+1, 27+26+20+19+16+15+11+3+1, 27+26+20+19+16+15+11+5+1, 27+26+20+19+16+15+12+11+1, 27+26+20+19+16+15+12+11+3+1, 27+26+20+19+16+15+12+11+5+1, 27+26+20+19+16+15+14, 27+26+22+1, 27+26+22+3+1, 27+26+22+5+1, 27+26+22+11+1, 27+26+22+11+3+1, 27+26+22+11+5+1, 27+26+22+12+11+1, 27+26+22+12+11+3+1, 27+26+22+12+11+5+1, 27+26+22+14, 27+26+22+16+1, 27+26+22+16+3+1, 27+26+22+16+5+1, 27+26+22+16+11+1, 27+26+22+16+11+3+1, 27+26+22+16+11+5+1, 27+26+22+16+12+11+1,

27+26+22+16+12+11+3+1, 27+26+22+16+12+11+5+1, 27+26+22+16+14, 27+26+22+16+15+1, 27+26+22+16+15+3+1, 27+26+22+16+15+5+1, 27+26+22+16+15+11+1, 27+26+22+16+15+11+3+1, 27+26+22+16+15+11+5+1, 27+26+22+16+15+12+11+1, 27+26+22+16+15+12+11+3+1, 27+26+22+16+15+12+11+5+1, 27+26+22+16+15+14, 27+26+22+20+1, 27+26+22+20+2+1, 27+26+22+20+3+1, 27+26+22+20+4+1, 27+26+22+20+5+1, 27+26+22+20+6+1, 27+26+22+20+7+1, 27+26+22+20+8+1, 27+26+22+20+9+1, 27+26+22+20+10+1, 27+26+22+20+11+1, 27+26+22+20+11+3+1, 27+26+22+20+11+5+1, 27+26+22+20+12+11+1, 27+26+22+20+12+11+3+1, 27+26+22+20+12+11+5+1, 27+26+22+20+13+11+1, 27+26+22+20+13+11+3+1, 27+26+22+20+13+11+5+1, 27+26+22+20+14, 27+26+22+20+15+1, 27+26+22+20+15+3+1, 27+26+22+20+15+5+1, 27+26+22+20+15+11+1, 27+26+22+20+15+11+3+1, 27+26+22+20+15+11+5+1, 27+26+22+20+15+12+11+1, 27+26+22+20+15+12+11+3+1, 27+26+22+20+15+12+11+5+1, 27+26+22+20+15+14, 27+26+22+20+16+1, 27+26+22+20+16+3+1, 27+26+22+20+16+5+1, 27+26+22+20+16+11+1, 27+26+22+20+16+11+3+1, 27+26+22+20+16+11+5+1, 27+26+22+20+16+12+11+1, 27+26+22+20+16+12+11+3+1, 27+26+22+20+16+12+11+5+2726+22+20+16+12+11+5+1, 27+26+22+20+16+14, 27+26+22+20+16+15+1, 27+26+22+20+16+15+3+1, 27+26+22+20+16+15+5+1, 27+26+22+20+16+15+11+1, 27+26+22+20+16+15+11+3+1, 27+26+22+20+16+15+11+5+1, 27+26+22+20+16+15+12+11+1, 27+26+22+20+16+15+12+11+3+1, 27+26+22+20+16+15+12+11+5+1, 27+26+22+20+16+15+14, 27+26+22+20+17+1, 27+26+22+20+17+3+1, 27+26+22+20+17+5+1, 27+26+22+20+17+11+1, 27+26+22+20+17+11+3+1, 27+26+22+20+17+11+5+1, 27+26+22+20+18+1, 27+26+22+20+18+3+1, 27+26+22+20+18+5+1, 27+26+22+20+18+11+1, 27+26+22+20+18+11+3+1, 27+26+22+20+18+11+5+1, 27+26+22+20+18+12+11+1, 27+26+22+20+18+12+11+3+1, 27+26+22+20+18+12+11+5+1, 27+26+22+20+18+14, 27+26+22+20+18+15+1, 27+26+22+20+18+15+3+1, 27+26+22+20+18+15+5+1, 27+26+22+20+18+15+11+1, 27+26+22+20+18+15+11+3+1, 27+26+22+20+18+15+11+5+1, 27+26+22+20+18+15+12+11+1, 27+26+22+20+18+15+12+11+3+1, 27+26+22+20+18+15+12+11+5+1, 27+26+22+20+18+15+14, 27+26+22+20+19+1, 27+26+22+20+19+3+1, 27+26+22+20+19+5+1, 27+26+22+20+19+11+1, 27+26+22+20+19+11+3+1, 27+26+22+20+19+11+5+1, 27+26+22+20+19+12+11+1, 27+26+22+20+19+12+11+3+1, 27+26+22+20+19+12+11+5+1, 27+26+22+20+19+14, 27+26+22+20+19+15+1, 27+26+22+20+19+15+3+1, 27+26+22+20+19+15+5+1, 27+26+22+20+19+15+11+1, 27+26+22+20+19+15+11+3+1, 27+26+22+20+19+15+11+5+1, 27+26+22+20+19+15+12+11+1, 27+26+22+20+19+15+12+11+3+1, 27+26+22+20+19+15+12+11+5+1, 27+26+22+20+19+15+14, 27+26+22+20+19+16+1, 27+26+22+20+19+16+3+1, 27+26+22+20+19+16+5+1, 27+26+22+20+19+16+11+1, 27+26+22+20+19+16+11+3+1, 27+26+22+20+19+16+11+5+1, 27+26+22+20+19+16+12+11+1, 27+26+22+20+19+16+12+11+3+1, 27+26+22+20+19+16+12+11+5+1, 27+26+22+20+19+16+14, 27+26+22+20+19+16+15+1, 27+26+22+20+19+16+15+3+1, 27+26+22+20+19+16+15+5+1, 27+26+22+20+19+16+15+11+1, 27+26+22+20+19+16+15+11+3+1, 27+26+22+20+19+16+15+11+5+1, 27+26+22+20+19+16+15+12+11+1, 27+26+22+20+19+16+15+12+11+3+1, 27+26+22+20+19+16+15+12+11+5+1, 27+26+22+20+19+16+15+14, 28+26+1, 28+26+3+1, 28+26+5+1, 28+26+11+1, 28+26+11+3+1, 28+26+11+5+1, 28+26+12+11+1, 28+26+12+11+3+1, 28+26+12+11+5+1, 28+26+14, 28+26+16+1, 28+26+16+3+1, 28+26+16+5+1, 28+26+16+11+1, 28+26+16+11+3+1, 28+26+16+11+5+1, 28+26+16+12+11+1, 28+26+16+12+11+3+1, 28+26+16+12+11+5+1, 28+26+16+14, 28+26+16+15+1, 28+26+16+15+3+1, 28+26+16+15+5+1, 28+26+16+15+11+1, 28+26+16+15+11+3+1, 28+26+16+15+11+5+1, 28+26+16+15+12+11+1, 28+26+16+15+12+11+3+1, 28+26+16+15+12+11+5+1, 28+26+16+15+14, 28+26+20+1, 28+26+20+2+1, 28+26+20+3+1, 28+26+20+4+1, 28+26+20+5+1, 28+26+20+6+1, 28+26+20+7+1, 28+26+20+8+1, 28+26+20+9+1, 28+26+20+10+1, 28+26+20+11+1, 28+26+20+11+3+1, 28+26+20+11+5+1, 28+26+20+12+11+1, 28+26+20+12+11+3+1, 28+26+20+12+11+5+1, 28+26+20+13+11+1, 28+26+20+13+11+3+1, 28+26+20+13+11+5+1, 28+26+20+14, 28+26+20+15+1, 28+26+20+15+3+1, 28+26+20+15+5+1, 28+26+20+15+11+1, 28+26+20+15+11+3+1, 28+26+20+15+11+5+1, 28+26+20+15+12+11+1, 28+26+20+15+12+11+3+1, 28+26+20+15+12+11+5+1, 28+26+20+15+14, 28+26+20+16+1, 28+26+20+16+3+1, 28+26+20+16+5+1, 28+26+20+16+11+1, 28+26+20+16+11+3+1, 28+26+20+16+11+5+1, 28+26+20+16+12+11+1, 28+26+20+16+12+11+3+1, 28+26+20+16+12+11+5+1, 28+26+20+16+14, 28+26+20+16+15+1, 28+26+20+16+15+3+1, 28+26+20+16+15+5+1, 28+26+20+16+15+11+1, 28+26+20+16+15+11+3+1, 28+26+20+16+15+11+5+1, 28+26+20+16+15+12+11+1, 28+26+20+16+15+12+11+3+1, 28+26+20+16+15+12+11+5+1, 28+26+20+16+15+14, 28+26+20+17+1, 28+26+20+17+3+1, 28+26+20+17+5+1, 28+26+20+17+11+2826+20+17+11+1, 28+26+20+17+11+3+1, 28+26+20+17+11+5+1, 28+26+20+18+1, 28+26+20+18+3+1, 28+26+20+18+5+1, 28+26+20+18+11+1, 28+26+20+18+11+3+1, 28+26+20+18+11+5+1, 28+26+20+18+12+11+1, 28+26+20+18+12+11+3+1, 28+26+20+18+12+11+5+1, 28+26+20+18+14, 28+26+20+18+15+1, 28+26+20+18+15+3+1, 28+26+20+18+15+5+1, 28+26+20+18+15+11+1, 28+26+20+18+15+11+3+1, 28+26+20+18+15+11+5+1, 28+26+20+18+15+12+11+1, 28+26+20+18+15+12+11+3+1, 28+26+20+18+15+12+11+5+1, 28+26+20+18+15+14, 28+26+20+19+1, 28+26+20+19+3+1, 28+26+20+19+5+1, 28+26+20+19+11+1, 28+26+20+19+11+3+1, 28+26+20+19+11+5+1, 28+26+20+19+12+11+1, 28+26+20+19+12+11+3+1, 28+26+20+19+12+11+5+1, 28+26+20+19+14, 28+26+20+19+15+1, 28+26+20+19+15+3+1, 28+26+20+19+15+5+1, 28+26+20+19+15+11+1, 28+26+20+19+15+11+3+1, 28+26+20+19+15+11+5+1, 28+26+20+19+15+12+11+1, 28+26+20+19+15+12+11+3+1, 28+26+20+19+15+12+11+5+1, 28+26+20+19+15+14, 28+26+20+19+16+1, 28+26+20+19+16+3+1, 28+26+20+19+16+5+1, 28+26+20+19+16+11+1, 28+26+20+19+16+11+3+1, 28+26+20+19+16+11+5+1, 28+26+20+19+16+12+11+1, 28+26+20+19+16+12+11+3+1, 28+26+20+19+16+12+11+5+28+26+20+19+16+12+11+5+1, 28+26+20+19+16+14, 28+26+20+19+16+15+1, 28+26+20+19+16+15+3+1, 28+26+20+19+16+15+5+1, 28+26+20+19+16+15+11+1, 28+26+20+19+16+15+11+3+1, 28+26+20+19+16+15+11+5+1, 28+26+20+19+16+15+12+11+1, 28+26+20+19+16+15+12+11+3+1, 28+26+20+19+16+15+12+11+5+1, 28+26+20+19+16+15+14, 28+26+22+1, 28+26+22+3+1, 28+26+22+5+1, 28+26+22+11+1, 28+26+22+11+3+1, 28+26+22+11+5+1, 28+26+22+12+11+1, 28+26+22+12+11+3+1, 28+26+22+12+11+5+1, 28+26+22+14, 28+26+22+16+1, 28+26+22+16+3+1, 28+26+22+16+5+1, 28+26+22+16+11+1, 28+26+22+16+11+3+1, 28+26+22+16+11+5+1, 28+26+22+16+12+11+1, 28+26+22+16+12+11+3+1, 28+26+22+16+12+11+5+1, 28+26+22+16+14, 28+26+22+16+15+1, 28+26+22+16+15+3+1, 28+26+22+16+15+5+1, 28+26+22+16+15+11+1, 28+26+22+16+15+11+3+1, 28+26+22+16+15+11+5+1, 28+26+22+16+15+12+11+1,

28+26+22+16+15+12+11+3+1, 28+26+22+16+15+12+11+5+1, 28+26+22+16+15+14, 28+26+22+20+1, 28+26+22+20+2+1, 28+26+22+20+3+1, 28+26+22+20+4+1, 28+26+22+20+5+1, 28+26+22+20+6+1, 28+26+22+20+7+1, 28+26+22+20+8+1, 28+26+22+20+9+1, 28+26+22+20+10+1, 28+26+22+20+11+1, 28+26+22+20+11+3+1, 28+26+22+20+11+5+1, 28+26+22+20+12+11+1, 28+26+22+20+12+11+3+1, 28+26+22+20+12+11+5+1, 28+26+22+20+13+11+1, 28+26+22+20+13+11+3+1, 28+26+22+20+13+11+5+1, 28+26+22+20+14, 28+26+22+20+15+1, 28+26+22+20+15+3+1, 28+26+22+20+15+5+1, 28+26+22+20+15+11+1, 28+26+22+20+15+11+3+1, 28+26+22+20+15+11+5+1, 28+26+22+20+15+12+11+1, 28+26+22+20+15+12+11+3+1, 28+26+22+20+15+12+11+5+1, 28+26+22+20+15+14, 28+26+22+20+16+1, 28+26+22+20+16+3+1, 28+26+22+20+16+5+1, 28+26+22+20+16+11+1, 28+26+22+20+16+11+3+1, 28+26+22+20+16+11+5+1, 28+26+22+20+16+12+11+1, 28+26+22+20+16+12+11+3+1, 28+26+22+20+16+12+11+5+1, 28+26+22+20+16+14, 28+26+22+20+16+15+1, 28+26+22+20+16+15+3+1, 28+26+22+20+16+15+5+1, 28+26+22+20+16+15+11+1, 28+26+22+20+16+15+11+3+1, 28+26+22+20+16+15+11+5+1, 28+26+22+20+16+15+12+11+1, 28+26+22+20+16+15+12+11+3+1, 28+26+22+20+16+15+12+11+5+1, 28+26+22+20+16+15+14, 28+26+22+20+17+1, 28+26+22+20+17+3+1, 28+26+22+20+17+5+1, 28+26+22+20+17+11+1, 28+26+22+20+17+11+3+1, 28+26+22+20+17+11+5+1, 28+26+22+20+18+1, 28+26+22+20+18+3+1, 28+26+22+20+18+5+1, 28+26+22+20+18+11+128+26+22+20+18+11+3+2826+22+20+18+11+3+1, 28+26+22+20+18+11+5+1, 28+26+22+20+18+12+11+1, 28+26+22+20+18+12+11+3+1, 28+26+22+20+18+12+11+5+1, 28+26+22+20+18+14, 28+26+22+20+18+15+1, 28+26+22+20+18+15+3+1, 28+26+22+20+18+15+5+1, 28+26+22+20+18+15+11+1, 28+26+22+20+18+15+11+3+1, 28+26+22+20+18+15+11+5+1, 28+26+22+20+18+15+12+11+1, 28+26+22+20+18+15+12+11+3+1, 28+26+22+20+18+15+12+11+5+1, 28+26+22+20+18+15+14, 28+26+22+20+19+1, 28+26+22+20+19+3+1, 28+26+22+20+19+5+1, 28+26+22+20+19+11+1, 28+26+22+20+19+11+3+1, 28+26+22+20+19+11+5+1, 28+26+22+20+19+12+11+1, 28+26+22+20+19+12+11+3+1, 28+26+22+20+19+12+11+5+1, 28+26+22+20+19+14, 28+26+22+20+19+15+1, 28+26+22+20+19+15+3+1, 28+26+22+20+19+15+5+1, 28+26+22+20+19+15+11+1, 28+26+22+20+19+15+11+3+1, 28+26+22+20+19+15+11+5+1, 28+26+22+20+19+15+12+11+1, 28+26+22+20+19+15+12+11+3+1, 28+26+22+20+19+15+12+11+5+1, 28+26+22+20+19+15+14, 28+26+22+20+19+16+1, 28+26+22+20+19+16+3+1, 28+26+22+20+19+16+5+1, 28+26+22+20+19+16+11+1, 28+26+22+20+19+16+11+3+1, 28+26+22+20+19+16+11+5+1, 28+26+22+20+19+16+12+11+1, 28+26+22+20+19+16+12+11+3+1, 28+26+22+20+19+16+12+11+5+1, 28+26+22+20+19+16+14, 28+26+22+20+19+16+15+1, 28+26+22+20+19+16+15+3+1, 28+26+22+20+19+16+15+5+1, 28+26+22+20+19+16+15+11+1, 28+26+22+20+19+16+15+11+3+1, 28+26+22+20+19+16+15+11+5+1, 28+26+22+20+19+16+15+12+11+1, 28+26+22+20+19+16+15+12+11+3+1, 28+26+22+20+19+16+15+12+11+5+1, 28+26+22+20+19+16+15+14, 38+1, 38+3+1, 38+5+1, 38+11+1, 38+11+3+1, 38+11+5+1, 38+12+11+1, 38+12+11+3+1, 38+12+11+5+1, 39+1, 39+3+1, 39+5+1, 39+11+1, 39+11+3+1, 39+11+5+1, 39+12+11+1, 39+12+11+3+1, 39+12+11+5+1, 39+14, 39+15+1, 39+15+3+1, 39+15+5+1, 39+15+11+1, 39+15+11+3+1, 39+15+11+5+1, 39+15+12+11+1, 39+15+12+11+3+1, 39+15+12+11+5+1, 39+15+14, 39+16+1, 39+16+3+1, 39+16+5+1, 39+16+11+1, 39+16+11+3+1, 39+16+11+5+1, 39+16+12+11+1, 39+16+12+11+3+1, 39+16+12+11+5+1, 39+16+14, 39+16+15+1, 39+16+15+3+1, 39+16+15+5+1, 39+16+15+11+1, 39+16+15+11+3+1, 39+16+15+11+5+1, 39+16+15+12+11+1, 39+16+15+12+11+3+1, 39+16+15+12+11+5+1, 39+16+15+14, 39+19+1, 39+19+3+1, 39+19+5+1, 39+19+11+1, 39+19+11+3+1, 39+19+11+5+1, 39+19+12+11+1, 39+19+12+11+3+1, 39+19+12+11+5+1, 39+19+14, 39+19+15+1, 39+19+15+3+1, 39+19+15+5+1, 39+19+15+11+1, 39+19+15+11+3+1, 39+19+15+11+5+1, 39+19+15+12+11+1, 39+19+15+12+11+3+1, 39+19+15+12+11+5+1, 39+19+15+14, 39+19+16+1, 39+19+16+3+1, 39+19+16+5+1, 39+19+16+11+1, 39+19+16+11+3+1, 39+19+16+11+5+1, 39+19+16+12+11+1, 39+19+16+12+11+3+1, 39+19+16+12+11+5+1, 39+19+16+14, 39+19+16+15+1, 39+19+16+15+3+1, 39+19+16+15+5+1, 39+19+16+15+11+1, 39+19+16+15+11+3+1, 39+19+16+15+11+5+1, 39+19+16+15+12+11+1, 39+19+16+15+12+11+3+1, 39+19+16+15+12+11+5+1, 39+19+16+15+14, 39+20+1, 39+20+2+1, 39+20+3+1, 39+20+4+1, 39+20+5+1, 39+20+6+1, 39+20+7+1, 39+20+8+1, 39+20+9+1, 39+20+10+1, 39+20+11+1, 39+20+11+3+1, 39+20+11+5+1, 39+20+12+11+1, 39+20+12+11+3+1, 39+20+12+11+5+1, 39+20+13+11+1, 39+20+13+11+3+1, 39+20+13+11+5+1, 39+20+14, 39+20+15+1, 39+20+15+3+1, 39+20+15+5+1, 39+20+15+11+1, 39+20+15+11+3+1, 39+20+15+11+5+1, 39+20+15+12+11+1, 39+20+15+12+11+3+1, 39+20+15+12+11+5+1, 39+20+15+14, 39+20+16+1, 39+20+16+3+1, 39+20+16+5+1, 39+20+16+11+1, 39+20+16+11+3+1, 39+20+16+11+5+1, 39+20+16+12+11+1, 39+20+16+12+11+3+1, 39+20+16+12+11+5+1, 39+20+16+14, 39+20+16+15+1, 39+20+16+15+3+1, 39+20+16+15+5+1, 39+20+16+15+11+1, 39+20+16+15+11+3+1, 39+20+16+15+11+5+1, 39+20+16+15+12+11+1, 39+20+16+15+12+11+3+1, 39+20+16+15+12+11+5+1, 39+20+16+15+14, 39+20+17+1, 39+20+17+3+1, 39+20+17+5+1, 39+20+17+11+1, 39+20+17+11+3+1, 39+20+17+11+5+1, 39+20+18+1, 39+20+18+3+1, 39+20+18+5+1, 39+20+18+11+1, 39+20+18+11+3+1, 39+20+18+11+5+1, 39+20+18+12+11+1, 39+20+18+12+11+3+1, 39+20+18+12+11+5+1, 39+20+18+14, 39+20+18+15+1, 39+20+18+15+3+1, 39+20+18+15+5+1, 39+20+18+15+11+1, 39+20+18+15+11+3+1, 39+20+18+15+11+5+1, 39+20+18+15+12+11+1, 39+20+18+15+12+11+3+1, 39+20+18+15+12+11+5+1, 39+20+18+15+14, 39+20+19+1, 39+20+19+3+1, 39+20+19+5+1, 39+20+19+11+1, 39+20+19+11+3+1, 39+20+19+11+5+1, 39+20+19+12+11+1, 39+20+19+12+11+3+1, 39+20+19+12+11+5+1, 39+20+19+14, 39+20+19+15+1, 39+20+19+15+3+1, 39+20+19+15+5+1, 39+20+19+15+11+1, 39+20+19+15+11+3+1, 39+20+19+15+11+5+1, 39+20+19+15+12+11+1, 39+20+19+15+12+11+3+1, 39+20+19+15+12+11+5+1, 39+20+19+15+14, 39+20+19+16+1, 39+20+19+16+3+1, 39+20+19+16+5+1, 39+20+19+16+11+1, 39+20+19+16+11+3+1, 39+20+19+16+11+5+1, 39+20+19+16+12+11+1, 39+20+19+16+12+11+3+1, 39+20+19+16+12+11+5+1, 39+20+19+16+14, 39+20+19+16+15+1, 39+20+19+16+15+3+1, 39+20+19+16+15+5+1, 39+20+19+16+15+11+1, 39+20+19+16+15+11+3+1, 39+20+19+16+15+11+5+1, 39+20+19+16+15+12+11+1, 39+20+19+16+15+12+11+3+1, 39+20+19+16+15+12+11+5+1, 39+20+19+16+15+14, 39+22+1, 39+22+3+1, 39+22+5+1, 39+22+11+1, 39+22+11+3+1, 39+22+11+5+1, 39+22+12+11+1, 39+22+12+11+3+1, 39+22+12+11+5+1, 39+22+14, 39+22+16+1, 39+22+16+3+1, 39+22+16+5+1, 39+22+16+11+1, 39+22+16+11+3+1, 39+22+16+11+5+1, 39+22+16+12+11+1, 39+22+16+12+11+3+1, 39+22+16+12+11+5+1, 39+22+16+14, 39+22+16+15+1, 39+22+16+15+3+1, 39+22+16+15+5+1, 39+22+16+15+11+1, 39+22+16+15+

11+3+1, 39+22+16+15+11+5+1, 39+22+16+15+12+11+1, 39+22+16+15+12+11+3+1, 39+22+16+15+12+11+5+1, 39+22+16+15+14, 39+22+20+1, 39+22+20+2+1, 39+22+20+3+1, 39+22+20+4+1, 39+22+20+5+1, 39+22+20+6+1, 39+22+20+7+1, 39+22+20+8+1, 39+22+20+9+1, 39+22+20+10+1, 39+22+20+11+1, 39+22+20+11+3+1, 39+22+20+11+5+1, 39+22+20+12+11+1, 39+22+20+12+11+3+1, 39+22+20+12+11+5+1, 39+22+20+13+11+1, 39+22+20+13+11+3+1, 39+22+20+13+11+5+1, 39+22+20+14, 39+22+20+15+1, 39+22+20+15+3+1, 39+22+20+15+5+1, 39+22+20+15+11+1, 39+22+20+15+11+3+1, 39+22+20+15+11+5+1, 39+22+20+15+12+11+1, 39+22+20+15+12+11+3+1, 39+22+20+15+12+11+5+1, 39+22+20+15+14, 39+22+20+16+1, 39+22+20+16+3+1, 39+22+20+16+5+1, 39+22+20+16+11+1, 39+22+20+16+11+3+1, 39+22+20+16+11+5+1, 39+22+20+16+12+11+1, 39+22+20+16+12+11+3+1, 39+22+20+16+12+11+5+1, 39+22+20+16+14, 39+22+20+16+15+1, 39+22+20+16+15+3+1, 39+22+20+16+15+5+1, 39+22+20+16+15+11+1, 39+22+20+16+15+11+3+1, 39+22+20+16+15+11+5+1, 39+22+20+16+15+12+11+1, 39+22+20+16+15+12+11+3+1, 39+22+20+16+15+12+11+5+1, 39+22+20+16+15+14, 39+22+20+17+1, 39+22+20+17+3+1, 39+22+20+17+5+1, 39+22+20+17+11+1, 39+22+20+17+11+3+1, 39+22+20+17+11+5+1, 39+22+20+18+1, 39+22+20+18+3+1, 39+22+20+18+5+1, 39+22+20+18+11+1, 39+22+20+18+11+3+1, 39+22+20+18+11+5+1, 39+22+20+18+12+11+1, 39+22+20+18+12+11+3+1, 39+22+20+18+12+11+5+1, 39+22+20+18+14, 39+22+20+18+15+1, 39+22+20+18+15+3+1, 39+22+20+18+15+5+1, 39+22+20+18+15+11+1, 39+22+20+18+15+11+3+1, 39+22+20+18+15+11+5+1, 39+22+20+18+15+12+11+1, 39+22+20+18+15+12+11+3+1, 39+22+20+18+15+12+11+5+1, 39+22+20+18+15+14, 39+22+20+19+1, 39+22+20+19+3+1, 39+22+20+19+5+1, 39+22+20+19+11+1, 39+22+20+19+11+3+1, 39+22+20+19+11+5+1, 39+22+20+19+12+11+1, 39+22+20+19+12+11+3+1, 39+22+20+19+12+11+5+1, 39+22+20+19+14, 39+22+20+19+15+1, 39+22+20+19+15+3+1, 39+22+20+19+15+5+1, 39+22+20+19+15+11+1, 39+22+20+19+15+11+3+1, 39+22+20+19+15+11+5+1, 39+22+20+19+15+12+11+1, 39+22+20+19+15+12+11+3+1, 39+22+20+19+15+12+11+5+1, 39+22+20+19+15+14, 39+22+20+19+16+1, 39+22+20+19+16+3+1, 39+22+20+19+16+5+1, 39+22+20+19+16+11+1, 39+22+20+19+16+11+3+1, 39+22+20+19+16+11+5+1, 39+22+20+19+16+12+11+1, 39+22+20+19+16+12+11+3+1, 39+22+20+19+16+12+11+5+1, 39+22+20+19+16+14, 39+22+20+19+16+15+1, 39+22+20+19+16+15+3+1, 39+22+20+19+16+15+5+1, 39+22+20+19+16+15+11+1, 39+22+20+19+16+15+11+3+1, 39+22+20+19+16+15+11+5+1, 39+22+20+19+16+15+12+11+1, 39+22+20+19+16+15+12+11+3+1, 39+22+20+19+16+15+12+11+5+1, 39+22+20+19+16+15+14, 40, 41.

In the list above, the numbers refer to the embodiments according to their numbering provided hereinabove whereas "+" indicates the dependency from another embodiment.

The different individualized embodiments are separated by commas. In other words, "11+3+1" for example refers to embodiment 11) depending on embodiment 3) depending on embodiment 1), i.e. embodiment "11+3+1" corresponds to embodiment 1) further limited by the features of the embodiments 3) and 11).

It is understood that a $P2Y_{12}$ receptor antagonist (notably Compound 1) that is described to be useful in the treatment or prevention of a disease according to any one of embodiments 1) to 38) is also useful in a method of treatment and/or prophylaxis of the disease wherein the method comprises the subcutaneous administration of a pharmaceutically active amount of the $P2Y_{12}$ receptor antagonist, or a pharmaceutically acceptable salt thereof, to a human subject in need thereof.

The present invention especially relates to a method for the emergency treatment of acute coronary syndromes (ACS) by patient self-administration prior to hospitalization of a pharmaceutically active amount of Compound 1, Ticagrelor or Ticagrelor-M (especially Compound 1), or a pharmaceutically acceptable salt thereof, wherein the method comprises the subcutaneous administration to the patient in need thereof.

The present invention also relates to a method for the treatment of a disease that is responsive to the inhibition of platelet activation and/or platelet aggregation comprising subcutaneous administration of a pharmaceutically active amount of Compound 1, Ticagrelor or Ticagrelor-M (especially Compound 1), or a pharmaceutically acceptable salt thereof, to a human subject in need thereof.

The present invention also relates to a method for the treatment of a disease that is responsive to a $P2Y_{12}$ receptor antagonist comprising subcutaneous administration of a pharmaceutically active amount of Compound 1, Ticagrelor or Ticagrelor-M (especially Compound 1), or a pharmaceutically acceptable salt thereof, to a human subject in need thereof.

The pharmaceutical composition comprising the $P2Y_{12}$ receptor antagonist (Compound 1, Ticagrelor, or Ticagrelor-M), or a pharmaceutically acceptable salt thereof, may be in the form of an aqueous or oily solution, suspension or emulsion (preferably an aqueous solution) and may optionally contain one or more additional excipients. An additional excipient may be for instance a pharmaceutically acceptable acid or base (to adjust the pH value of the pharmaceutical composition) or a pharmaceutically acceptable salt such as sodium chloride (to adapt the tonicity of the pharmaceutical composition).

The pharmaceutical composition may be in the form of a ready-to-use solution, suspension or emulsion or in the form of a powder for injection comprising the $P2Y_{12}$ receptor antagonist, wherein the powder for injection requires reconstitution in a pharmaceutically acceptable liquid to give the aqueous or oily solution, suspension or emulsion prior to subcutaneous administration. The said solid may be in crystalline or amorphous form or in any mixture thereof.

The general terms and expressions used hereinbefore and/or hereinafter preferably have, within this disclosure, the following meanings:

The term "acute coronary syndromes" (ACS) refers to syndromes due to sudden decreased or interruption of blood flow in some coronary arteries. Acute coronary syndromes encompass ST elevation myocardial infarction (STEMI), non ST elevation myocardial infarction (NSTEMI) or unstable angina. It is understood that a $P2Y_{12}$ receptor antagonist that is disclosed to be useful in the prevention or treatment of ACS is likewise useful in the prevention or treatment of STEMI, NSTEMI and/or unstable angina.

The term "emergency treatment of suspected acute coronary syndromes" refers to a treatment of a patient wherein the patient shows symptoms of ACS such as suddenly occurring chest pain, chest discomfort (intermittent or not), persistent retrosternal pressure or heaviness radiating to the left arm, neck, back or jaw lasting for at least 10 min, nausea/vomiting, shortness of breath, fatigue, palpitations, lightheadedness or syncope (and notably clear symptoms of ACS such as suddenly occurring chest pain, chest discomfort (intermittent or not), or persistent retrosternal pressure or heaviness radiating to the left arm, neck, back or jaw lasting for at least 10 min); and wherein the patient is to be treated and/or requires treatment before an electrocardiogram, a chest X-ray and/or blood tests could be performed. In one embodiment, the patient is a patient who was already known to have a high risk to suffer from ACS before the symptoms (notably clear symptoms) of ACS occurred, such as for instance a patient with a known coronary artery disease who had a prior symptomatic episode of acute coronary syndromes. In a further embodiment, the treatment is effected by patient self-administration before hospitalization; it is preferred that the patient has received a training by a health care professional to better assess the symptoms of ACS before any such self-administration.

The term "coronary artery disease" (CAD) refers to a group of diseases that includes myocardial infarction, unstable angina, stable angina and sudden cardiac death.

The term "a patient who had a prior symptomatic episode of acute coronary syndromes" refers to a patient who had a myocardial infarction (STEMI or NSTEMI) or an unstable angina.

The term "subcutaneous administration" refers to an administration of a pharmaceutical composition into the subcutis by injection. Typical administration sites are the outer area of the upper arm, the abdomen (avoiding the area close to the umbilicus), the front of the thigh, the thorax, the neck, the upper back and the upper area of the buttock; preferred are the abdomen and the front of the thigh. A subcutaneous administration can be performed using any kind of a suitable injection device such as for instance a syringe or an autoinjector device.

The term "intradermal administration" refers to an administration of a pharmaceutical composition into the dermis by injection. Typical administration sites are the inner surface of the forearm and the upper back, under the scapula.

The term "bolus injection" if used in the context of a subcutaneous administration/injection refers to an injection of a discrete amount of a $P2Y_{12}$ receptor antagonist (notably in a pharmaceutical composition suitable for subcutaneous administration) within a relatively short period of time (typically between 1 sec to 90 sec).

The term "patient" refers to a mammal, especially a human, having a disease or disorder that can be prevented or treated with a $P2Y_{12}$ receptor antagonist. In a preferred embodiment, a patient is a human having a disease or disorder that can be prevented or treated (especially treated) with a $P2Y_{12}$ receptor antagonist wherein said human was already known before to have a statistically increased risk to develop the disease or disorder.

The term "patient self-administration" refers the administration of a pharmaceutical composition to a patient by the patient himself/herself or by an acquaintance having minimal medical training, such as a relative, a friend or a neighbour (and especially by the patient himself/herself).

The term "administration by a health care professional" refers to the administration of a pharmaceutical composition to a patient by a person who is professionally trained to perform such administrations such as for instance a nurse or a physician. It is preferred that any such administration is performed prior to hospitalization of the patient (e.g. in the ambulance or at any other place before the patient reaches the hospital).

The term "autoinjector device" refers to a medical device for automated injection of a pharmaceutical composition after pressing a trigger or an activator or the like. Autoinjector devices may be for instance in the form of a pen device, a patch device or a patch pump.

Any reference to a $P2Y_{12}$ receptor antagonist in this specification is to be understood as referring also to the pharmaceutically acceptable salts of such a $P2Y_{12}$ receptor antagonist. The term "pharmaceutically acceptable salt" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example 'Handbook of Pharmaceutical Salts. Properties, Selection and Use.', P. Heinrich Stahl, Camille G. Wermuth (Eds.), Wiley-VCH, 2008 and 'Pharmaceutical Salts and Co-crystals', Johan Wouters and Luc Quéré (Eds.), RSC Publishing, 2012.

A preferred pharmaceutically acceptable salt of Compound 1 is a hydrochloride salt of Compound 1. Another preferred pharmaceutically acceptable salt of Compound 1 is a 2-amino-2-(hydroxymethyl)-1,3-propanediol or a sodium salt of Compound 1.

The term "pharmaceutically acceptable liquid" refers to a liquid that gives an injectable solution, suspension or emulsion (especially a solution) if admixed with the $P2Y_{12}$ receptor antagonist (especially Compound 1), or a pharmaceutically acceptable salt thereof, optionally together with one or more therapeutically inert excipient(s), and that exhibits minimal undesired toxicological effects. A preferred example for a pharmaceutically acceptable liquid is water, especially water for injection and notably sterile water for injection.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Whenever the word "between" is used to describe a numerical range, it is to be understood that the end points of the indicated range are explicitly included in the range. For example: if a volume range is described to be between 0.1 mL and 3.0 mL, this means that the end points 0.1 mL and 3.0 mL are included in the range; or if a variable is defined as being an integer between 1 and 4, this means that the variable is the integer 1, 2, 3, or 4.

EXPERIMENTAL PART

Abbreviations:
The following abbreviations are used throughout the specification and the examples:
ACS Acute coronary syndromes
aq. Aqueous
ET External temperature
FACS Fluorescence-activated cell sorting
h hour(s)
IPC In-process control
IT Internal temperature
min Minute(s)
PBS Phosphate-buffered saline
PCI Percutaneous coronary intervention
PEG 400 Poly(ethylene glycol)
RT Room temperature
sat. saturated
sec second(s)
vol. L solvent per kg starting material Preparation of Compound 1 and its HCl Salt:

Compound 1 may be prepared according to the procedures as disclosed in WO 2009/069100 (example 2) or Caroff E et al., *J. Med. Chem.* (2015), 58, 9133-9153. Alternatively, Compound 1 and its HCl salt may be prepared according to the following procedure:

A 15 L reactor was charged with sodium (S)-6-(3-methoxypyrrolidin-1-yl)-2-phenylpyrimidine-4-carboxylate (584 g, 1.82 mol) and 1-hydroxy-benzotriazole mono hydrate (HOBt) (274 g, 1.1 eq.). Water (1305 mL, 2.0 vol.) was added. The pH of the suspension was 5-6. Butyl (R)-4-(2-amino-3-(diethoxyphosphoryl)propanoyl)piperazine-1-carboxylate (665.7 g, 1.0 eq) was dissolved in tetrahydrofurane (THF) (1960 ml, 3.0 vol.). The solution was added to the reaction at 20-30° C. during 5-10 min. A solution of 1-ethyl-3-(3-dimethylaminopropyl)carbodiimide (EDCI) (389 g, 1.2 eq.) in water (1305 ml, 2.0 vol.) was added to the reaction at 20-30° C. during 15-30 min. The pH of the reaction stayed between 6-7. The reaction was stirred during 4 h at 20-30° C. An IPC showed 93% conversion. The reaction was diluted with dichloromethane (DCM) (3265 ml, 5.0 vol.) and ½ sat. aq. sodium hydrogencarbonat solution (3265 ml, 5.0 vol.). The layers were separated. The organic layer was washed again with ½ sat. aq. sodium hydrogencarbonat solution (3265 ml, 5.0 vol.). The layers were separated. An IPC showed the complete removal of HOBt. The organic layer was washed with aq. 10% citric acid (3265 ml, 5.0 vol.). In total 3.75 L of solvents were distilled off at minimal 800 mbar and ET=75-80° C. during 40 min. The residual solution was cooled to 20-30° C. Aq. 32% HCl (3 L, 19 eq.) was added during 5-10 min at 20-30° C. An IPC after 4 h of stirring showed complete hydrolysis. Water (5.2 L, 8 vol.) was added at 20-30° C. The reaction was diluted with DCM (5.2 L, 8 vol.). The layers were separated. The aqueous layer was extracted again 2× with DCM (5.2 L, 8 vol.). All DCM layers were combined and filtered through a polycap 75 HD filter. In total 14 L of solvents were distilled off during 2 h at atmospheric pressure and ET=75-80° C. Acetone (21.6 L, 33 vol.) was added to the refluxing reaction mixture at ET=70-75° C. To the refluxing fine suspension water (325 mL, 0.5 vol.) was added. The fine, pale suspension was stirred at reflux during 1.5 h and a thick white slurry was obtained. The slurry was cooled to IT=25° C. during 1 h (ramp). The solid product was isolated by filtration. The filter cake was rinsed with acetone (4.5 L, 7 vol.) and was dried by blowing nitrogen through it to give 750 g (69%) of ((R)-3-(4-(butoxycarbonyl)piperazin-1-yl)-2-(6-((S)-3-methoxypyrrolidin-1-yl)-2-phenylpyrimidine-4-carboxamido)-3-oxopropyl)phosphonic acid hydrochloride as a white solid. The LC MS purity was >99% a/a, the 1H-NMR assay purity was 98% w/w.

Formulation of Compound 1 (Lower Dose of 1 mg/mL):

An aqueous solution of 2-amino-2-(hydroxymethyl)-1,3-propanediol (Tris base, 21.6 mL, 1.0 M) was added to 4.80 L Water for Injection (WFI) in a glass vessel. 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (6.00 g) and mannitol (210 g) were added successively and the mixture was stirred until complete dissolution. Additional Tris base was added to pH=7.4±0.1. The solution was diluted to a final volume of 6.00 L with WFI, refilled into glass vials (1.1 mL per vial), dried by lyophilisation and reconstituted prior to administration with 1.0 mL WFI to give a solution of Compound 1 for subcutaneous administration.

Formulation of Compound 1 (Higher Dose of 20 mg/mL):

An aqueous solution of 2-amino-2-(hydroxymethyl)-1,3-propanediol (Tris base, 21.6 mL, 1.0 M) was added to 4.80 L Water for Injection (WFI) in a glass vessel. 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester hydrochloride (120 g) and mannitol (120 g) were added successively and the mixture was stirred until complete dissolution. Additional Tris base was added to pH=7.4±0.1. The solution was diluted to a final volume of 6.00 L with WFI, refilled into glass vials (1.1 mL per vial), dried by lyophilisation and reconstituted prior to administration with 1.0 mL WFI to give a solution of Compound 1 for subcutaneous administration.

In-Vivo Measurements of Time Dependent Platelet Inhibition after Subcutaneous Administration of $P2Y_{12}$ Receptor Antagonists:

Animals:

Male Balb/c mice were purchased from Charles River laboratories (Sulzfeld, Germany). All animals were maintained under identical conditions in accordance with the guidelines of the Basel-Landschaft cantonal veterinary office. Husbandry was accomplished in professional animal housing facilities, which provided group-cages, standard diet/water ad libitum, and standard illumination and climate conditions. The technical assistants performed at least one inspection per day. Sufficient time was provided for the animals to be accustomed to the experimental environment. Stress reduction was provided also by enrichment of cages, and providing the possibility to retire to dark housings (taking advantage of the color blindness of albino mice in the red range of the light spectrum). Inside the red housing the animals have the impression of being in the dark, while this housing remains visible to normal human vision.

Reagents:

The hydrochloride salt of Compound 1 was synthesized according to the above mentioned procedure. Ticagrelor was extracted from commercially available tablets (Brilique).

Fibrinogen from Human Plasma Alexa Fluor™ 488 conjugate, catalogue number F-13191 was purchased from Molecular Probes and handled as described on provider's data sheet.

Preparation of test compounds: Compound 1 hydrochloride (0.04 mg/mL), Ticagrelor (0.2 mg/mL), Elinogrel (6 mg/mL) or Cangrelor (0.04 mg/mL) were dissolved in 25% PEG 400/water.

Experimental Groups:

Compounds were administrated by subcutaneous injection on the lower abdomen:

Compound 1 hydrochloride, 0.2 mg/kg (respectively 5 mL/kg)

Ticagrelor, 1 mg/kg (respectively 5 mL/kg)

Elinogrel, 30 mg/kg (respectively 5 mL/kg)

Cangrelor, 0.2 mg/kg (respectively 5 mL/kg)

Animal Preparation:

After an acclimatization period of at least 7 days, mice were anesthetized with Isoflurane (2-5%). The animals were then placed on a thermostatically-controlled heating table to maintain body temperature at 36-38° C. A polyurethane catheter (BTPU-027) was inserted into the right jugular vein and advanced into the vena cava for infusion of Heparin and to collect blood. In order to perform accurate platelet assays it is necessary to ensure that the blood collection does not lead to platelet activation. Therefore Heparin (4000 U/kg/2.5 mL) was intravenously injected to prevent blood from coagulation.

Experimental Procedure:

Two minutes after the injection of Heparin, 60 µL of whole blood was collected via the vena cava catheter (baseline). After the baseline blood sampling the test compounds were subcutaneously injected on the lower abdomen of the animals. 10, 20, 30, 40 and 60 minutes after the subcutaneous injection of the test compounds, 60 µL of whole blood were collected via the vena cava catheter for the fibrinogen binding assay.

AF488-Fibrinogen Binding Assay:

This assay is particularly well adapted for reliable studies of the effect of $P2Y_{12}$ antagonists on mouse platelets under in vitro and in vivo conditions. The assay allows to measure ADP-induced AF488-Fibrinogen binding on mouse platelets in only 6 µL whole blood and without washing steps.

The blood was first incubated with 4 µL vehicle or 4 µL Compound 1 hydrochloride (to give 2 µM final concentration in diluted blood) for 15 minutes at RT. This concentration of Compound 1 hydrochloride was determined in prior experiments to inhibit 100% of ADP-induced AF488-Fibrinogen binding on platelets and represents the nonspecific signal. Next, 10 µL of AF488-Fibrinogen (to give 0.5 mg/mL final concentration) were added followed by incubation of 5 minutes. To induce AF488-Fibrinogen binding, the platelets were then incubated with 10 µL ADP (to give 20 µM final concentration) for 5 minutes. In addition, an incubation with a platelet specific Allophycocyanin (APC) anti-Mouse CD61 (integrin beta 3) antibody (clone 2C9.G2) was performed for 10 minutes. The platelets were then fixed by addition of 34 µL cold paraformaldehyde solution (to give 0.1% final concentration) and stored at 4° C. for about 20 minutes. The samples were finally diluted with 1.8 mL cold PBS and put on hold at 4° C. for at least 2 hours, time necessary for gently red blood cell lysis, before measuring by flow cytometry.

Data Acquisition:

Flow cytometry was performed using a FACSCanto II instrument (BD Bioscience). The setting of fluorescence compensation was not required due to the use of two different lasers.

Platelets were first detected using the platelet specific fluorescence signal of APC-CD61 (APC-settings for fluorescence emission peak at 660 nm). The platelet population was then gated using forward-scatter (FSC) and side-scatter (SSC) and their FITC-labeled Fibrinogen signal (FITC-settings for fluorescence emission peak at 525 nm) was quantitated as Mean Fluorescence Intensity (MFI) of 5000 platelets. For each sample, the MFI from corresponding nonspecific sample was subtracted.

TABLE 1

Mean Fluorescence Intensities of AF488-Fibrinogen binding to platelets

| | Time [Minutes] | | | | |
|---|---|---|---|---|---|
| | 0 [MFI] | 10 [MFI] | 20 [MFI] | 40 [MFI] | 60 [MFI] |
| Compound 1 0.2 mg/kg s.c. | | | | | |
| Experiment 1 | 6037 | | 1721 | 1229 | 1315 |
| Experiment 2 | 9042 | | 2909 | 2542 | 2544 |
| Experiment 3 | 8234 | | 1655 | 1126 | 997 |
| Experiment 4 | 7711 | 2509 | 1697 | 1495 | 1235 |
| Experiment 5 | 10574 | 4175 | 2882 | 2638 | 1914 |
| Experiment 6 | 13675 | 5806 | 3763 | 2582 | 2375 |
| Ticagrelor mg/kg s.c. | | | | | |
| Experiment 1 | 8449 | | 3351 | 1576 | 1067 |
| Experiment 2 | 5864 | | 911 | 510 | 554 |
| Experiment 3 | 8707 | | 3061 | 970 | 549 |
| Experiment 4 | 8218 | 2001 | 1224 | 683 | 917 |
| Experiment 5 | 6904 | 6537 | 4292 | 2181 | 1761 |
| Experiment 6 | 11749 | 5771 | 3473 | 2340 | 2261 |
| Experiment 7 | 6073 | 5625 | 3840 | 1937 | 1148 |
| Elinogrel 30 mg/kg s.c. | | | | | |
| Experiment 1 | 8124 | 4403 | 2374 | 1644 | 2034 |
| Experiment 2 | 5370 | 4712 | 3847 | 1768 | 1503 |
| Experiment 3 | 7045 | 3842 | 2177 | 1652 | 1515 |
| Experiment 4 | 7097 | 3840 | 4078 | 2619 | 2191 |
| Cangrelor 0.2 mg/kg s.c. | | | | | |
| Experiment 1 | 6200 | 1596 | 713 | 765 | 1048 |
| Experiment 2 | 7453 | 1628 | 1364 | 732 | 682 |
| Experiment 3 | 5476 | 2550 | 1012 | 921 | 961 |

In-Vivo Measurements of Time Dependent Inhibition of Platelet Aggregation (IPA) after Subcutaneous Administration of Compound 1 to Healthy Volunteers:

The time- and dose-dependency of plasma concentration and inhibition of platelet aggregation (IPA) after subcutaneous administration of Compound 1 was investigated in a clinical phase I study in healthy male subjects.

Study Design:

In a randomized, double-blind, placebo-controlled study, 48 subjects in fasted condition were exposed to single, subcutaneous doses ranging from 1 to 32 mg (1 mg, 2 mg, 4 mg, 8 mg, 16 mg and 32 mg) of Compound 1 (n=6 on Compound 1 and n=2 on placebo per dose level).

Subcutaneous Formulation of Compound 1:

Compound 1 for s.c. administration was available as sealed glass vials at the strength of 20 mg. The vials contained lyophilized Compound 1 to be reconstituted with 1 mL of water for injection to prepare stock solutions of 20 mg/mL (see above: Formulation of Compound 1 (higher dose of 20 mg/mL)). These stock solutions were further diluted with 0.9% sodium chloride to prepare 2, 4, 8, 16, and 20 mg/mL solutions. The volume injected was 0.5 mL for dose levels 1, 2, 4, and 8 mg. For dose levels 16 and 32 mg, 1 or 2 injection(s) of 0.8 mL from the 20 mg/mL solution was (were) performed.

The solution for injection was prepared for administration in a syringe suitable for s.c. injection. The solution was administered as injection(s) in the thigh.

Assessment of Pharmacokinetic (PK) Parameters:

The plasma PK parameters of Compound 1 were derived by non-compartmental analysis of the plasma concentration-time profiles. The following parameters were obtained: maximum plasma concentration ($C_{max}$); time to reach $C_{max}$ ($t_{max}$); area under the plasma concentration-time curve (AUC) from zero to time t of the last measured concentration above the limit of quantification ($AUC_{0-t}$); and terminal elimination half-life ($t_{1/2}$).

1) Blood Sampling

Blood was collected by direct venipuncture or via an i.v. catheter placed in an antecubital vein in the arm in a 4 mL Monovette® or equivalent tube containing ethylene diamine tetra-acetic acid. Immediately following collection of the required blood volume, the Monovettes® were slowly tilted backwards and forwards (no shaking) to bring the anticoagulant into solution, and immediately cooled on ice. Within 30 min of collection, the Monovettes® were centrifuged at approximately 1500 g for 10 min at 4° C. The plasma was transferred into one labeled polypropylene tube to avoid carry-over of erythrocytes. All samples were stored in an upright position below −70° C.

2) Bioanalysis

The analysis of Compound 1 in plasma was performed using a validated liquid chromatography coupled to tandem mass spectrometry assay. The lower limit of quantification (LLOQ) was 1 ng/mL. Concentrations were calculated by interpolation from a calibration curve. Quality control (QC) samples were analyzed throughout the study. Their measured concentrations were used to determine between-run and overall precision and accuracy of the analysis.

3) Results were discarded, and, thereafter, blood was drawn gently into two open 3.5 mL collection tubes. Collection tubes for LTA (light transmission aggregometry) assays contained phenylalanine-proline-arginine-cholormethylketone (PPACK) as an anticoagulant.

2) Bioanalysis

Adenosine diphosphate (ADP)-induced platelet aggregation was evaluated by a LTA assay measuring platelet-induced aggregation as an increase in light transmittance (Michelson A D, Methods for the measurement of platelet function (2009) Am J Cardiol 103(3):20A-26A).

LTA assay: The two 3.5 mL blood samples were centrifuged to prepare platelet-rich plasma (PRP) and platelet-poor plasma (PPP). If needed, PRP was adjusted to a final platelet count of $260 \times 10^9$ platelets per liter by dilution with PPP from the same donor. The assay was performed with an 8-channel platelet aggregometer, recording the aggregation

TABLE 2

Summary table of pharmacokinetic parameters of Compound 1 following subcutaneous doses of 1 to 32 mg

| Parameter [unit] | 1 mg (N = 6) | 2 mg (N = 6) | 4 mg (N = 6) | 8 mg (N = 6) | 16 mg (N = 6) | 32 mg (N = 6) |
|---|---|---|---|---|---|---|
| $C_{max}$ [ng/mL] | | | | | | |
| G.M. | 33.654 | 58.437 | 128.394 | 272.731 | 435.035 | 929.632 |
| 95% CI | 25.4, 44.7 | 48.5, 70.4 | 76.5, 215 | 211, 353 | 335, 565 | 786, 1100 |
| $t_{max}$ [h] | | | | | | |
| Median | 0.500 | 0.500 | 0.500 | 0.500 | 0.750 | 0.750 |
| Min, Max | 0.25, 1.00 | 0.42, 1.00 | 0.37, 1.00 | 0.33, 1.00 | 0.25, 1.00 | 0.50, 1.00 |
| $AUC_{0-t}$ [ng * h/mL] | | | | | | |
| G.M. | 56.053 | 115.599 | 260.652 | 585.336 | 1119.438 | 2343.485 |
| 95% CI | 45.3, 69.4 | 89.8, 149 | 181, 375 | 449, 763 | 951, 1317 | 1956, 2807 |
| $t_{1/2}$ [h] | | | | | | |
| G.M. | 1.337 | 1.916 | 2.663 | 3.975 | 7.204 | 9.203 |
| 95% CI | 1.09, 1.64 | 1.18, 3.11 | 2.02, 3.51 | 2.38, 6.63 | 4.89, 10.6 | 6.15, 13.8 |

G.M.: geometric mean;
95% CI: 95% confidence interval of geometric mean

Assessment of Pharmacodynamic (PD) Parameters (Inhibition of Platelet Aggregation):

1) Blood Sampling

PD blood samples were collected by direct venipuncture or via an i.v. catheter placed in an antecubital vein in the arm, using 18-21 gauge needles. The first 2 mL of blood after addition of 20 μM ADP as agonist for 6 min. The results are expressed as percent change in light transmittance at maximum (peak) platelet aggregation (MPA), calculated relative to the baseline signal of 0%. The measurements were performed in duplicate.

3) Results

TABLE 3

Summary table of pharmacodynamic parameters (% IPA (inhibition of platelet aggregation) calculated using maximum platelet aggregation values) following subcutaneous doses of 1 to 32 mg

| Time [h] | 1 mg (N = 6) mean ± SD | 2 mg (N = 6) mean ± SD | 4 mg (N = 6) mean ± D | 8 mg (N = 6) mean ± SD | 16 mg (N = 6) mean ± SD | 32 mg (N = 6) mean ± SD |
|---|---|---|---|---|---|---|
| 0.25 | 61.4 ± 15.1 | 60.3 ± 48.3 | 79.7 ± 6.0 | 88.9 ± 8.4 | 92.8 ± 5.5 | 95.5 ± 2.7 |
| 0.5 | 64.4 ± 12.8 | 79.5 ± 10.8 | 84.7 ± 5.4 | 90.0 ± 8.5 | 93.1 ± 3.6 | 94.5 ± 2.0 |
| 3 | 15.8 ± 20.0 | 36.8 ± 30.0 | 58.5 ± 7.2 | 77.9 ± 19.5 | 95.0 ± 1.2 | 94.5 ± 2.0 |
| 4 | −10.0 ± 24.2 | 35.5 ± 18.9 | 50.6 ± 22.1 | 70.9 ± 12.5 | 88.2 ± 4.7 | 91.2 ± 1.9 |
| 5 | −6.1 ± 26.0 | 14.1 ± 28.4 | 47.9 ± 17.9 | 75.2 ± 11.5 | 87.6 ± 5.5 | 92.1 ± 2.6 |
| 12 | −4.5 ± 24.7 | 31.3 ± 28.9 | 37.4 ± 16.7 | 64.0 ± 10.4 | 76.0 ± 13.8 | 83.5 ± 12.9 |
| 48 | −47.7 ± 29.9 | 11.3 ± 38.5 | 2.1 ± 16.3 | −1.3 ± 33.7 | −1.6 ± 43.8 | 29.8 ± 20.9 |

SD: standard deviation

As can be seen from Table 3, at each dose level, peak % IPA was achieved within approximately 15-30 min post dosing. Peak % IPA exceeded 85% at doses ≥4 mg (at doses ≥8 mg even in less than 15 min). The duration of PD effects was dose-dependent. Mean % IPA≥85% was sustained for approximately 5 h and 12 h post administration of 16 mg and 32 mg Compound 1, respectively.

The invention claimed is:

1. A method for the prevention or treatment of a disease selected from acute coronary syndromes, myocardial infarction, peripheral ischaemia, amaurosis, sudden cardiac death, ischaemic stroke and transient ischaemic attack, the method comprising administering a pharmaceutically effective amount of a P2Y12 receptor antagonist, or a pharmaceutically acceptable salt thereof, to a patient in need thereof; wherein the $P2Y_{12}$ receptor antagonist is 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester; and wherein the $P2Y_{12}$ receptor antagonist is administered to the patient by intradermal or subcutaneous administration.

2. The method according to claim 1, wherein the disease is selected from acute coronary syndromes and myocardial infarction.

3. The method according to claim 1, wherein the P2Y12 receptor antagonist is administered prior to hospitalization.

4. The method according to claim 3, wherein the P2Y12 receptor antagonist is administered by patient self-administration.

5. A method for the emergency treatment of suspected acute coronary syndromes, the method comprising administering a pharmaceutically effective amount of a P2Y12 receptor antagonist, or a pharmaceutically acceptable salt thereof, by patient self-administration prior to hospitalization; wherein the $P2Y_{12}$ receptor antagonist is 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester; and wherein the $P2Y_{12}$ receptor antagonist is administered to the patient by intradermal or subcutaneous administration.

6. The method according to claim 1, wherein the $P2Y_{12}$ receptor antagonist is administered to a patient by subcutaneous administration.

7. The method according to claim 1, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 1 mg and 75 mg per administration.

8. The method according to claim 1, wherein the P2Y12 receptor antagonist is administered in a bolus injection.

9. The method according to claim 1, wherein an inhibition of platelet aggregation of at least 75% is reached within 30 min after onset of administration of the $P2Y_{12}$ receptor antagonist in at least 80% of the patients.

10. A method for the emergency treatment of acute coronary syndromes by patient self-administration prior to hospitalization of a pharmaceutically active amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester, or a pharmaceutically acceptable salt thereof, wherein the method comprises the subcutaneous administration to the patient in need thereof.

11. The method according to claim 5, wherein the $P2Y_{12}$ receptor antagonist is administered to a patient by subcutaneous administration.

12. The method according to claim 5, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 1 mg and 75 mg per administration.

13. The method according to claim 5, wherein the $P2Y_{12}$ receptor antagonist is administered in a bolus injection.

14. The method according to claim 5, wherein an inhibition of platelet aggregation of at least 75% is reached within 30 min after onset of administration of the $P2Y_{12}$ receptor antagonist in at least 80% of the patients.

15. The method according to claim 2, wherein the $P2Y_{12}$ receptor antagonist is administered prior to hospitalization.

16. The method according to claim 15, wherein the $P2Y_{12}$ receptor antagonist is administered by patient self-administration.

17. The method according to claim 2, wherein the $P2Y_{12}$ receptor antagonist is administered to a patient by subcutaneous administration.

18. The method according to claim 3, wherein the $P2Y_{12}$ receptor antagonist is administered to a patient by subcutaneous administration.

19. The method according to claim 15, wherein the $P2Y_{12}$ receptor antagonist is administered to a patient by subcutaneous administration.

20. The method according to claim 16, wherein the $P2Y_{12}$ receptor antagonist is administered to a patient by subcutaneous administration.

21. The method according to claim 3, wherein the amount of 44(R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 1 mg and 75 mg per administration.

22. The method according to claim 15, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 1 mg and 75 mg per administration.

23. The method according to claim 2, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 5 mg and 35 mg per administration.

24. The method according to claim 3, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 5 mg and 35 mg per administration.

25. The method according to claim 5, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 5 mg and 35 mg per administration.

26. The method according to claim 19, wherein the amount of 4(R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 5 mg and 35 mg per administration.

27. The method according to claim 20, wherein the amount of 4(R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 5 mg and 35 mg per administration.

28. The method according to claim 10, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is comprised between 5 mg and 35 mg per administration.

29. The method according to claim 2, wherein the $P2Y_{12}$ receptor antagonist is administered in a bolus injection.

30. The method according to claim 3, wherein the $P2Y_{12}$ receptor antagonist is administered in a bolus injection.

31. The method according to claim 26, wherein the $P2Y_{12}$ receptor antagonist is administered in a bolus injection.

32. The method according to claim 27, wherein the $P2Y_{12}$ receptor antagonist is administered in a bolus injection.

33. The method according to claim 28, wherein the $P2Y_{12}$ receptor antagonist is administered in a bolus injection.

34. The method according to claim 2, wherein an inhibition of platelet aggregation of at least 80% is reached within 30 min after onset of administration of the $P2Y_{12}$ receptor antagonist in at least 80% of the patients.

35. The method according to claim 3, wherein an inhibition of platelet aggregation of at least 80% is reached within 30 min after onset of administration of the $P2Y_{12}$ receptor antagonist in at least 80% of the patients.

36. The method according to claim 5, wherein an inhibition of platelet aggregation of at least 80% is reached within 30 min after onset of administration of the $P2Y_{12}$ receptor antagonist in at least 80% of the patients.

37. The method according to claim 19, wherein an inhibition of platelet aggregation of at least 80% is reached within 30 min after onset of administration of the $P2Y_{12}$ receptor antagonist in at least 80% of the patients.

38. The method according to claim 20, wherein an inhibition of platelet aggregation of at least 80% is reached within 30 min after onset of administration of the $P2Y_{12}$ receptor antagonist in at least 80% of the patients.

39. The method according to claim 26, wherein an inhibition of platelet aggregation of at least 80% is reached within 30 min after onset of administration of the $P2Y_{12}$ receptor antagonist in at least 80% of the patients.

40. The method according to claim 27, wherein an inhibition of platelet aggregation of at least 80% is reached within 30 min after onset of administration of the $P2Y_{12}$ receptor antagonist in at least 80% of the patients.

41. The method according to claim 28, wherein an inhibition of platelet aggregation of at least 80% is reached within 30 min after onset of administration of the $P2Y_{12}$ receptor antagonist in at least 80% of the patients.

42. The method according to claim 2, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

43. The method according to claim 3, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

44. The method according to claim 5, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

45. The method according to claim 17, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

46. The method according to claim 19, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

47. The method according to claim 20, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

48. The method according to claim 10, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

49. The method according to claim 34, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

50. The method according to claim 36, wherein the amount of 4-((R)-2-{[6-((S)-3-methoxy-pyrrolidin-1-yl)-2-phenyl-pyrimidine-4-carbonyl]-amino}-3-phosphono-propionyl)-piperazine-1-carboxylic acid butyl ester that is administered is 16 mg per administration.

* * * * *

UNITED STATES PATENT AND TRADEMARK OFFICE
CERTIFICATE OF CORRECTION

PATENT NO. : 11,179,390 B2
APPLICATION NO. : 16/494254
DATED : November 23, 2021
INVENTOR(S) : Martine Baumann et al.

It is certified that error appears in the above-identified patent and that said Letters Patent is hereby corrected as shown below:

In the Specification

In Column 1 below the title, please add the following:
Cross Reference to Related Applications
This application is a United States Application under 35 U.S.C. 371 claiming benefit of PCT Application No. PCT/EP2018/056372, filed on March 14, 2018, which claims the benefit of PCT Application No. PCT/EP2017/056175, filed on March 15, 2017, the contents of each of which are incorporated herein by reference.

Column 2, Line 12:
"(2010) J Am Coil Cardiol 55:2446-2455). Furthermore,"
Should read:
(2010) J Am Coll Cardiol 55:2446-2455). Furthermore, Column 2, Line 24:
"Coil Cardiol 56:1456-1462; Wiviott S D et al. (2007)"
Should read:
Coll Cardiol 56:1456-1462; Wiviott S D et al. (2007)

Column 2, Line 30:
"Interv 5:268-277; Parodi G et al. (2013) J Am Coil Cardiol"
Should read:
Interv 5:268-277; Parodi G et al. (2013) J Am Coll Cardiol Column 13, Lines 32-33:
"24+20+16+15+5+1, 24+20+16+15+5+1, 24+20+16±15±11±3+1, 24+20+16+15+11+5+1, 24+20+16+15+"
Should read:
24+20+16+15+5+1, 24+20+16+15+11+1, 24+20+16+15+11+3+1, 24+20+16+15+11+5+1, 24+20+16+15+

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*

Column 18, Lines 3-6:
"27+26+12+11+5+1, 27+26+1, 27+26+12+11+5+1, 27+2614, 27+26+16+1, 27+26+16+3+1, 27+26+16+5+1, 27+26+16+11+1, 27+26+16+11+3+1, 2726±16±11±5±1, 27+26±16±12+11±1, 27+26+16+12+11+3+1, 27+26+16+"
Should read:
27+26+12+11+5+1, 27+26+14, 27+26+16+1, 27+26+16+3+1, 27+26+16+5+1, 27+26+16+11+1, 27+26+16+11+3+1, 27+26+16+11+5+1, 27+26+16+12+11+1, 27+26+16+12+11+3+1, 27+26+16+

Column 18, Line 34:
"20+18+5+1, 27+26+20+18+11+1, 27+26+20+18++11+1,"
Should read:
20+18+5+1, 27+26+20+18+11+1, Column 18, Lines 41-43:
"18+15+12+11+3+127+26+20+18+15+12+11+5+1, 27+26+20+18+15+14, 27+26+20+18+15+12+11+5+1, 27+26+20+18+15+14, 27+26+20+19+1, 27+26+20+19+3+1, 27+26+"
Should read:
18+15+12+11+3+1, 27+26+20+18+15+12+11+5+1, 27+26+20+18+15+14, 27+26+20+19+1, 27+26+20+19+3+1, 27+26+

Column 18, Line 51:
"2726+20+19+15+12+11+5+1, 27+26+20+19+15+14,"
Should read:
27+26+20+19+15+12+11+5+1, 27+26+20+19+15+14, Column 19, Lines 23-24:
"12+11+3+1, 27+26+22+20+16+12+11+5+2726+22+20+16+12+11+5+1, 27+26+22+20+16+14, 27+26+22+20+16+"
Should read:
12+11+3+1, 27+26+22+20+16+12+11+5+1, 27+26+22+20+16+14, 27+26+22+20+16+

Column 20, Line 28:
"28+26+20+17+11+2826+20+17+11+1, 28+26+20+17+11+"
Should read:
28+26+20+17+11+1, 28+26+20+17+11+

Column 20, Lines 50-51:
"12+11+1, 28+26+20+19+16+12+11+3+1, 28+26+20+19+16+12+11+5+28+26+20+19+16+12+11+5+1, 28+26+20+"
Should read:
12+11+1, 28+26+20+19+16+12+11+3+1, 28+26+20+19+16+12+11+5+1, 28+26+20+

Column 21, Lines 29-30:
"28+26+22+20+18+5+1, 28+26+22+20+18+11+128+26+22+20+18+11+3+2826+22+20+18+11+3+1, 28+26+22+"

Should read:
28+26+22+20+18+5+1, 28+26+22+20+18+11+1, 28+26+22+20+18+11+3+1, 28+26+22+

Column 22, Line 23:
"39+20+12+11+5+1, 39+20+13+11+1, 39+20+13++11+3+1,"
Should read:
39+20+12+11+5+1, 39+20+13+11+1, 39+20+13+11+3+1, Column 30, Table 1, Line 9:
"mg/kg s.c."
Should read:
1 mg/kg s.c.

In the Claims

Claim 21, Column 34, Line 28:
"of 44(R)-2-{[6-((S)-3-methoxy-pyrrolidin-1-yl)-2-phenyl-"
Should read:
of 4-((R)-2-{[6-((S)-3-methoxy-pyrrolidin-1-yl)-2-phenyl- Claim 26, Column 34, Line 54:
"amount of 4(R)-2-{[6-((S)-3-methoxy-pyrrolidin-1-yl)-2-"
Should read:
amount of 4-((R)-2-{[6-((S)-3-methoxy-pyrrolidin-1-yl)-2-

Claim 27, Column 34, Line 60:
"amount of 4(R)-2-{[6-((S)-3-methoxy-pyrrolidin-1-yl)-2-"
Should read:
amount of 4-((R)-2-{[6-((S)-3-methoxy-pyrrolidin-1-yl)-2-

Claim 28, Column 35, Line 1:
"pionyl)-piperazine-1-carb oxylic acid butyl ester that is"
Should read:
pionyl)-piperazine-1-carboxylic acid butyl ester that is Claim 42, Column 36, Line 3:
"pyrim idine-4-carbonyl]-amino }-3-phosphono-propionyl)-"
Should read:
pyrimidine-4-carbonyl]-amino}-3-phosphono-propionyl)-

Claim 43, Column 36, Line 8:
"pyrim idine-4-carbonyl]-amino}-3-phosphono-propionyl)-"
Should read:
pyrimidine-4-carbonyl]-amino}-3-phosphono-propionyl)-

CERTIFICATE OF CORRECTION (continued)
U.S. Pat. No. 11,179,390 B2

Claim 44, Column 36, Line 13:
"pyrim idine-4-carbonyl]-amino}-3-phosphono-propionyl)-"
Should read:
pyrimidine-4-carbonyl]-amino}-3-phosphono-propionyl)-

Claim 45, Column 36, Line 18:
"phenyl-pyrim idine-4-carbonyl]-amino}-3-phosphono-pro-"
Should read:
phenyl-pyrimidine-4-carbonyl]-amino}-3-phosphono-pro- Claim 46, Column 36, Line 23:
"phenyl-pyrim idine-4-carbonyl]-amino}-3-phosphono-pro-"
Should read:
phenyl-pyrimidine-4-carbonyl]-amino}-3-phosphono-pro- Claim 47, Column 36, Line 28:
"phenyl-pyrim idine-4-carbonyl]-amino}-3-phosphono-pro-"
Should read:
phenyl-pyrimidine-4-carbonyl]-amino}-3-phosphono-pro- Claim 48, Column 36, Line 33:
"phenyl-pyrim idine-4-carbonyl]-amino}-3-phosphono-pro-"
Should read:
phenyl-pyrimidine-4-carbonyl]-amino}-3-phosphono-pro- Claim 49, Column 36, Line 38:
"phenyl-pyrim idine-4-carbonyl]-amino}-3-phosphono-pro-"
Should read:
phenyl-pyrimidine-4-carbonyl]-amino}-3-phosphono-pro- Claim 50, Column 36, Line 43:
"phenyl-pyrim idine-4-carbonyl]-amino}-3-phosphono-pro-"
Should read:
phenyl-pyrimidine-4-carbonyl]-amino}-3-phosphono-pro-